(12) United States Patent
Broderick et al.

(10) Patent No.: US 11,266,341 B2
(45) Date of Patent: Mar. 8, 2022

(54) MEASURING DYNAMIC BODY MOVEMENT

(71) Applicant: Beneufit, Inc., Kentfield, CA (US)

(72) Inventors: Jeffery Broderick, San Anselmo, CA (US); Douglas Van Blaricom, San Pablo, CA (US); Jerome Lisk, Tyler, TX (US); Zenan Li, Guangzhou (CN); Sukhad Anand, New Delhi (IN)

(73) Assignee: Beneufit, Inc., Kentfield, CA (US)

( * ) Notice: Subject to any disclaimer, the term of this patent is extended or adjusted under 35 U.S.C. 154(b) by 0 days.

(21) Appl. No.: 17/314,191

(22) Filed: May 7, 2021

(65) Prior Publication Data

US 2022/0007993 A1    Jan. 13, 2022

Related U.S. Application Data

(63) Continuation of application No. 16/948,936, filed on Oct. 6, 2020, now abandoned, which is a continuation
(Continued)

(51) Int. Cl.
*A61B 5/00* (2006.01)
*A61B 5/11* (2006.01)
(Continued)

(52) U.S. Cl.
CPC .......... *A61B 5/4082* (2013.01); *A61B 5/1079* (2013.01); *A61B 5/1101* (2013.01);
(Continued)

(58) Field of Classification Search
CPC ... A61B 5/4082; A61B 5/1101; A61B 5/1079; A61B 5/112; A61B 5/4842;
(Continued)

(56) References Cited

U.S. PATENT DOCUMENTS

| | | |
|---|---|---|
| 2012/0154618 A1 | 6/2012 | Markovic et al. |
| 2013/0190093 A1 | 7/2013 | Wohlstadter et al. |

(Continued)

FOREIGN PATENT DOCUMENTS

WO    2019079489    4/2019

OTHER PUBLICATIONS

U.S. Appl. No. 16/163,238, filed Oct. 17, 2018, Measuring Body Movement in Movement Disorder Disease.
(Continued)

*Primary Examiner* — Christopher Wait
(74) *Attorney, Agent, or Firm* — Schwegman Lundberg & Woessner, P.A.

(57) ABSTRACT

In one example, a system for measuring body movement in a movement disorder disease is provided. The system may comprise at least one processor and a memory storing processor executable codes, which, when implemented by the at least one processor, cause the system to perform operations comprising, at least receiving a video including a sequence of images and detecting at least one object of interest in one or more of the images. Feature reference points of the at least one object of interest are located, and a virtual movement-detection framework is generated in one or more of the images. The operations may include detecting, over the sequence of images, at least one singular or reciprocating movement of the feature reference point relative to the virtual movement-detection framework and generating a virtual path tracking a path of the at least one detected singular or reciprocating movement of the feature reference point.

20 Claims, 33 Drawing Sheets

Related U.S. Application Data of application No. 16/163,238, filed on Oct. 17, 2018, now abandoned.

(60) Provisional application No. 62/573,236, filed on Oct. 17, 2017.

(51) Int. Cl.
    *A61B 5/107*     (2006.01)
    *G06K 9/00*     (2006.01)
    *G06T 7/00*     (2017.01)
    *G06T 7/246*     (2017.01)

(52) U.S. Cl.
CPC .......... *A61B 5/112* (2013.01); *G06K 9/00268* (2013.01); *G06K 9/00342* (2013.01); *G06K 9/00355* (2013.01); *G06T 7/0012* (2013.01); *G06T 7/246* (2017.01); *A61B 5/1112* (2013.01); *A61B 5/1124* (2013.01); *A61B 5/1128* (2013.01); *A61B 5/4842* (2013.01); *A61B 2562/0219* (2013.01); *G06T 2207/30004* (2013.01); *G06T 2207/30201* (2013.01)

(58) Field of Classification Search
CPC .......... A61B 5/1112; A61B 2562/0219; A61B 5/1128; A61B 5/1124; G06K 9/00268; G06K 9/00342; G06K 9/00355; G06T 7/0012; G06T 7/246; G06T 2207/30004; G06T 2207/30201
See application file for complete search history.

(56) References Cited

U.S. PATENT DOCUMENTS

| | | | | |
|---|---|---|---|---|
| 2014/0371544 | A1* | 12/2014 | Wu | ........................ G16H 40/67 600/301 |
| 2015/0286858 | A1* | 10/2015 | Shaburov | ................ G10L 25/63 382/103 |
| 2016/0089073 | A1 | 3/2016 | Tafazzoli et al. | |
| 2017/0262599 | A1* | 9/2017 | Grisel | .................. A61B 5/7282 |
| 2019/0110736 | A1 | 4/2019 | Broderick et al. | |
| 2019/0142328 | A1 | 5/2019 | Broderick et al. | |

OTHER PUBLICATIONS

U.S. Appl. No. 16/249,453, filed Jan. 16, 2019, Measuring Dynamic Body Movement.
U.S. Appl. No. 16/948,936, filed Oct. 6, 2020, Measuring Dynamic Body Movement.
"International Application Serial No. PCT US2018 056337, International Search Report dated Dec. 20, 2018", 2 pages.
"International Application Serial No. PCT US2018 056337, Written Opinion dated Dec. 20, 2018", 6 pages.
"U.S. Appl. No. 16/163,238, Non Final Office Action dated Apr. 6, 2020", 17 pages.
"International Application Serial No. PCT US2018 056337, International Preliminary Report on Patentability dated Apr. 30, 2020", 8 pages.
"U.S. Appl. No. 16/249,453, Non Final Office Action dated May 29, 2020", 13 pages.

* cited by examiner

MEASURING DYNAMIC BODY MOVEMENT

CLAIM OF PRIORITY

This application is a continuation of and claims the benefit of priority of U.S. application Ser. No. 16/948,936, filed Oct. 6, 2020, which is a continuation of U.S. application Ser. No. 16/163,238, filed Oct. 17, 2018, which claims the benefit of priority to U.S. Provisional Application Ser. No. 62/573,236, filed on Oct. 17, 2017, which is incorporated herein by reference in its entirety.

TECHNICAL FIELD

The subject matter disclosed herein generally relates to technical improvements and improved machines in measuring body movement in movement disorder disease and, in some examples, to body movement disorder monitoring systems and methods.

BACKGROUND

Movement disorders lack diagnostic biomarkers that identify the disease state and rate of progression. Instead, neurologists meet patients in person and perform a battery of subjective tests to determine a disease state and recommend an appropriate treatment plan.

A treatment dilemma thus exits. Due to the location of their residence or inability to travel, many patients with movement disorders such as Parkinson's disease (PD) do not have access to a movement disorders specialist. Those who do have access typically see their neurologist no more than once in every six months. Standard therapy titration relies on a repeated process of clinical assessment at the office and patient interviews. For many patients, this infrequent interaction with their treating physician means that they endure suboptimal treatments for extended periods.

Complex medication regimens, intraday symptom fluctuations and cognitive issues make managing the disease a challenge for People (or Person) with Parkinson's (PwP) and their caregivers. Current objective diagnostic sensors and other tools have cost and logistical barriers. They are marketed to healthcare professionals and researchers, not PwP who are left to manage their disease with inadequate tools.

Biopharma companies developing drugs for some diseases such as Tardive Dyskinesia (TD) and Parkinson's dyskinesia are forced to rely on suboptimal outcome measures such as the Abnormal Involuntary Movement Scale (AIMS) score and The Unified Dyskinesia Rating Scale (UDysRS). Promising new medications have failed because human error, subjectivity and language and cultural issues related to these rating scales cloud clinical trial results.

The Unified Parkinson's Disease Rating Scale (UPDRS) is a scale that was developed for Parkinson's Disease (also termed PD herein) as an effort to incorporate elements from existing scales to provide a comprehensive but efficient and flexible means to monitor PD-related disability and impairment. The development of the UPDRS involved multiple trial versions, and the final published scale is known as MDS-UPDRS. The scale itself has four components, largely derived from preexisting scales that were reviewed and modified by a consortium of movement disorders specialists (Part I, Mentation, Behavior and Mood; Part II, Activities of Daily Living; Part III, Motor; Part IV, Complications). The UPDRS is frequently utilized and for multiple purposes, including clinical practice. The UPDRS is an acknowledged standard in measuring disease progression and to measure the clinical improvement of FDA approved medications in clinical trials.

Several articles have been published on scoring variability with the UPDRS. As with any scale scoring, symptoms vary from rater to rater. This variability can make it difficult to assess the impact of improvement of medications in clinical trials which cost millions of dollars. Interrater reliability (IRR) has been studied and found to vary in movement disorder specialists versus other providers (general neurologists, neurologist with other subspecialties, nurses, non-neurologists, etc.). IRR among movement disorder specialists has been studied by the International Parkinson's and Movement Disorder Society. The rates of successful certification on the motor section of the Unified Parkinson's Disease Rating Scale (UPDRS) after training with the UPDRS Teaching Tape was published in 2004.

In this study only one-half of two hundred and twenty-six raters that participated successfully completed certification on their first attempt, but all completed by the third attempt. North American raters scored better than Europeans raters. The most difficult case to rate was the subject with the least impairment. Standardized methods for training UPDRS application are essential to ensure that raters use the scale uniformly. Raters have the greatest difficulty with the mildest impairment, making training especially important to a study of early PD. Furthermore, at UPDRS live training sessions there are always raters that have a 1- to 3-point difference in scoring even when rating the same patient video.

The present disclosure seeks to address these significant technical and medical drawbacks by providing improved technology, as described further below, aimed at solving these problems.

SUMMARY

In some embodiments, there is provided a system for measuring body movement in movement disorder disease, the system comprising a computing device including at least one processor and a memory storing processor executable codes, which, when implemented by the at least one processor, cause the system to perform the steps of: receiving a video including a sequence of images; detecting at least one object of interest in one or more of the images; locating feature reference points of the at least one object of interest; generating a virtual movement-detection framework in one or more of the images; aligning the virtual movement-detection framework with the at least one object of interest in one or more of the images based at least in part on a feature reference point; detecting, in real-time, over the sequence of images, at least one singular or reciprocating movement of the feature reference point relative to the virtual movement-detection framework; generating a virtual path tracking a path of the at least one detected movement of the feature reference point; analyzing at least coordinates of the virtual path or feature reference point and associating the detected at least one movement with a body movement disorder selected from a plurality of body movement disorders; generating or presenting a disorder status of an individual based on the associated body movement disorder selected from the plurality of body movement disorders; and generating a communication including data associated with the disorder status based on or including a trend in the disorder status.

Some embodiments of the present inventive subject matter include methods for measuring body movement in movement disorder disease. In one example, a method comprises: receiving a video including a sequence of images; detecting at least one object of interest in one or more of the images; locating feature reference points of the at least one object of interest; generating a virtual movement-detection framework in one or more of the images; aligning the virtual movement-detection framework with the at least one object of interest in one or more of the images based at least in part on a feature reference point; detecting, in real-time, over the sequence of images, at least one singular or reciprocating movement of the feature reference point relative to the virtual movement-detection framework; generating a virtual path tracking a path of the at least one detected movement of the feature reference point; analyzing at least coordinates of the virtual path or feature reference point and associating the detected at least one movement with a body movement disorder selected from a plurality of body movement disorders; generating or presenting a disorder status of an individual based on the associated body movement disorder selected from the plurality of body movement disorders; and generating a communication including data associated with the disorder status based on or including a trend in the disorder status.

Some embodiments may include machine-readable media including instructions which, when read by a machine, cause the machine to perform the operations of any one or more of the methodologies described herein.

BRIEF DESCRIPTION OF THE DRAWINGS

Some embodiments are illustrated by way of example and not limitation in the figures of the accompanying drawings that appear below.

DETAILED DESCRIPTION

Figure 1:
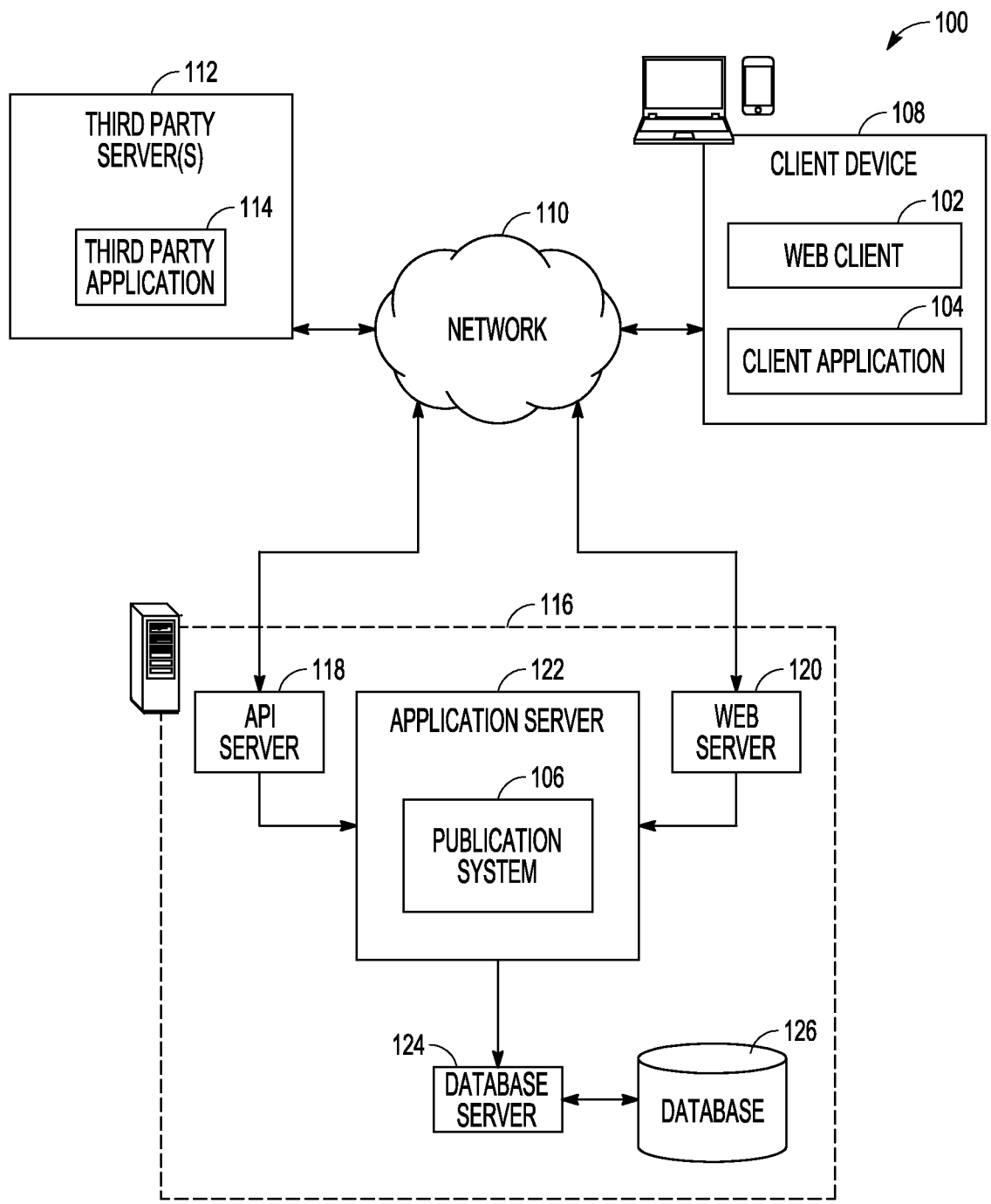
FIG. 1 is a block diagram illustrating a networked system, according to an example embodiment.

"Carrier Signal" in this context refers to any intangible medium that is capable of storing, encoding, or carrying instructions for execution by the machine, and includes digital or analog communications signals or other intangible medium to facilitate communication of such instructions. Instructions may be transmitted or received over the network using a transmission medium via a network interface device and using any one of a number of well-known transfer protocols.

"Client Device" in this context refers to any machine that interfaces to a communications network to obtain resources from one or more server systems or other client devices. A client device may be, but is not limited to, a mobile phone, desktop computer, laptop, portable digital assistants (PDAs), smart phones, tablets, ultra-books, netbooks, laptops, multi-processor systems, microprocessor-based or programmable consumer electronics, game consoles, set-top boxes, or any other communication device that a user may use to access a network.

"Communications Network" in this context refers to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"Component" in this context refers to a device, physical entity or logic having boundaries defined by function or subroutine calls, branch points, application program interfaces (APIs), or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components.

A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an Application Specific Integrated Circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors.

It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"Machine-Readable Medium" in this context refers to a component, device or other tangible media able to store instructions and data temporarily or permanently and may include, but not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"Processor" in this context refers to any circuit or virtual circuit (a physical circuit emulated by logic executing on an actual processor) that manipulates data values according to control signals (e.g., "commands", "op codes", "machine code", etc.) and which produces corresponding output signals that are applied to operate a machine. A processor may, for example, be a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC) or any combination thereof. A processor may further be a multi-core processor having two or more independent processors (sometimes referred to as "cores") that may execute instructions contemporaneously.

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2017-2018, Beneufit, Inc., All Rights Reserved.

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

With reference to FIG. 1, an example embodiment of a high-level SaaS network architecture 100 is shown. A networked system 116 provides server-side functionality via a network 110 (e.g., the Internet or wide area network (WAN)) to a client device 108. A web client 102 and a programmatic client, in the example form of an application 104, are hosted and execute on the client device 108. The networked system 116 includes an application server 122, which in turn hosts a publication system 106 (e.g. a publication platform hosted at https://dash.beneufit.com/) that provides a number of functions and services to the application 104 that accesses the networked system 116. The application 104 also provides a number of interfaces described herein, which present output of the scheduling operations to a user of the client device 108.

The client device 108 enables a user to access and interact with the networked system 116, and ultimately the publication system 106. For instance, the user provides input (e.g., touch screen input or alphanumeric input) to the client device 108, and the input is communicated to the networked system 116 via the network 110. In this instance, the networked system 116, in response to receiving the input from the user, communicates information back to the client device 108 via the network 110 to be presented to the user.

An Application Program Interface (API) server 118 and a web server 120 are coupled, and provide programmatic and web interfaces respectively, to the application server 122. The application server 122 hosts the publication system 106, which includes components or applications described further below. The application server 122 is, in turn, shown to be coupled to a database server 124 that facilitates access to information storage repositories (e.g., a database 126). In an example embodiment, the database 126 includes storage devices that store information accessed and generated by the publication system 106. The database 126 may include a real-time database as described elsewhere herein.

Additionally, a third-party application 114, executing on a third-party server(s) 112, is shown as having programmatic access to the networked system 116 via the programmatic interface provided by the Application Program Interface (API) server 118. For example, the third-party application 114, using information retrieved from the networked system 116, may support one or more features or functions on a website hosted by the third party.

Turning now specifically to the applications hosted by the client device 108, the web client 102 may access the various systems (e.g., publication system 106) via the web interface supported by the web server 120. Similarly, the application 104 (e.g., an "app" such as PDFit) accesses the various services and functions provided by the publication system 106 via the programmatic interface provided by the Application Program Interface (API) server 118. The application 104 may be, for example, an "app" executing on a client device 108, such as an iOS or Android OS application to enable a user to access and input data on the networked system 116 in an off-line manner, and to perform batch-mode communications between the programmatic client application 104 and the networked system networked system 116.

Further, while the SaaS network architecture 100 shown in FIG. 1 employs a client-server architecture, the present inventive subject matter is not limited to such an architecture, and could equally well find application in a distributed, or peer-to-peer, architecture system, for example. The publication system 106 could also be implemented as a stand-alone software program, which does not necessarily have networking capabilities.

Figure 2:
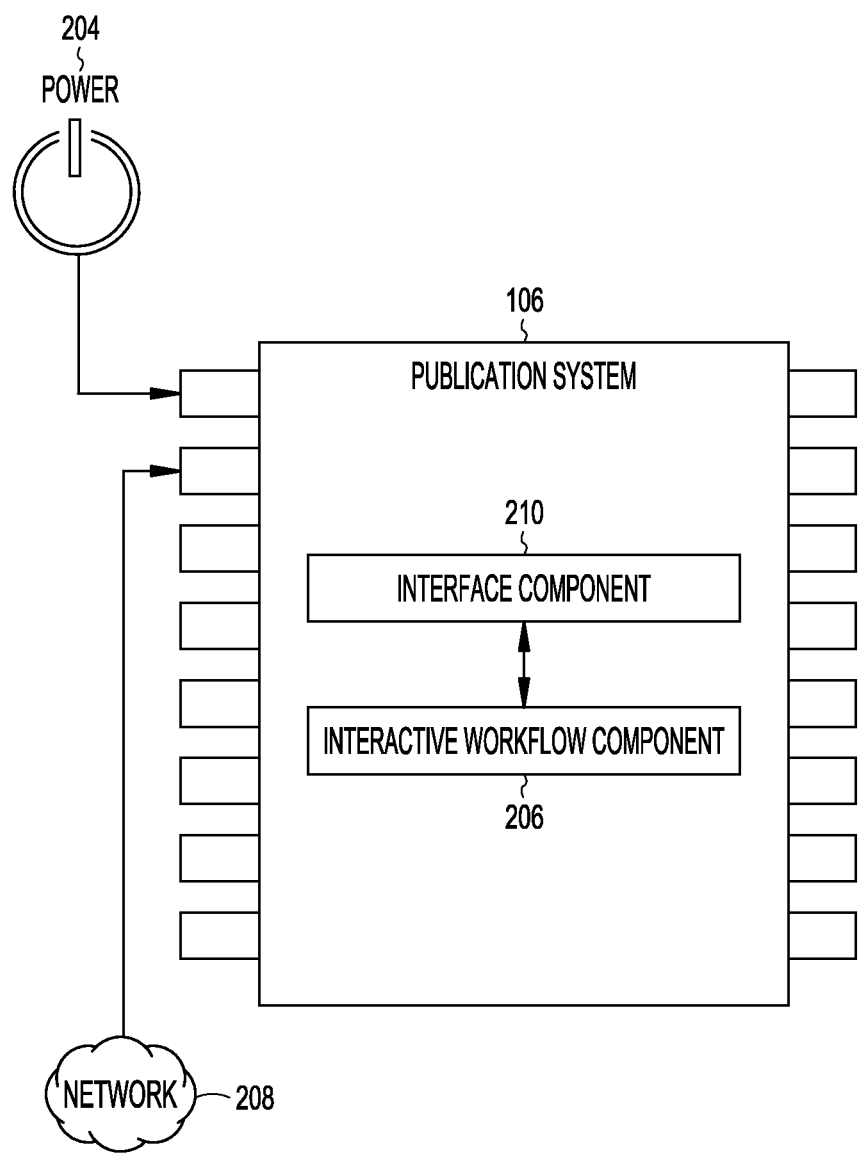
FIG. 2 is a block diagram showing for the architectural details of a publication system, according to some example embodiments.

FIG. 2 is a block diagram showing architectural details of a publication system 106, according to some example embodiments. Specifically, the publication system 106 is shown to include an interface component 210 by which the publication system 106 communicates (e.g., over the network 208) with other systems within the SaaS network architecture 100.

The interface component 210 is communicatively coupled to an interactive workflow component 206 that operates, in conjunction with a real-time database 126, to provide multiscreen interactive workflow facilitation services in accordance with the methods described further below with reference to the accompanying drawings.

Figure 3:
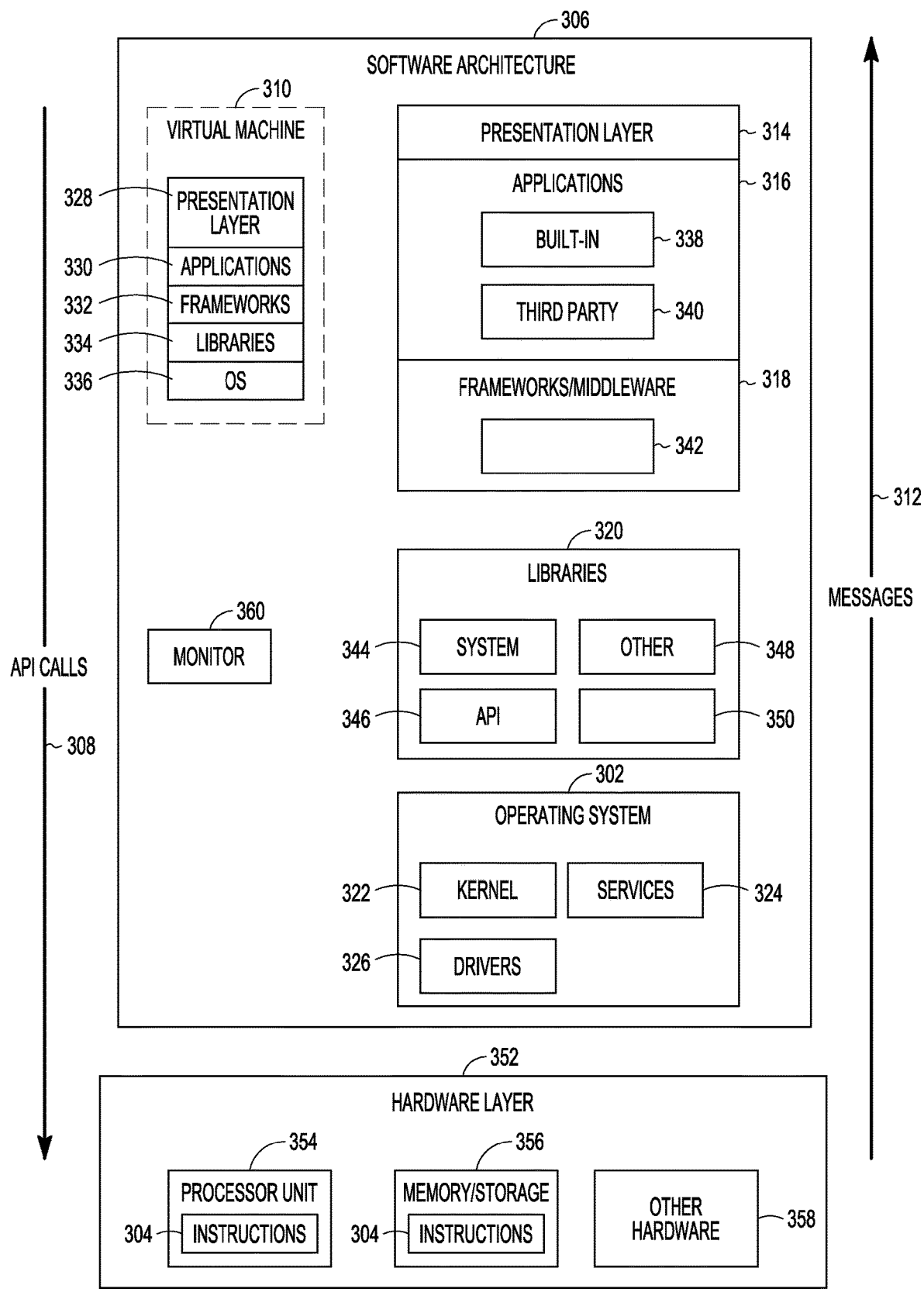
FIG. 3 is a block diagram illustrating a representative software architecture, which may be used in conjunction with various hardware architectures herein described.

FIG. 3 is a block diagram illustrating an example software architecture 306, which may be used in conjunction with various hardware architectures herein described. FIG. 3 is a non-limiting example of a software architecture 306 and it will be appreciated that many other architectures may be implemented to facilitate the functionality described herein. The software architecture 306 may execute on hardware such as machine 400 of FIG. 4 that includes, among other things, processors 404, memory/storage 406, and I/O components 418. A representative hardware layer 352 is illustrated and can represent, for example, the machine 400 of FIG. 4. The representative hardware layer 352 includes a processing unit 354 having associated executable instructions 304. Executable instructions 304 represent the executable instructions of the software architecture 306, including implementation of the methods, components and so forth described herein. The hardware layer 352 also includes memory and/or storage modules as memory/storage 356, which also have executable instructions 304. The hardware layer 352 may also comprise other hardware 358.

In the example architecture of FIG. 3, the software architecture 306 may be conceptualized as a stack of layers where each layer provides particular functionality. For example, the software architecture 306 may include layers such as an operating system 302, libraries 320, applications 316 and a presentation layer 314. Operationally, the applications 316 and/or other components within the layers may invoke application programming interface (API) API calls 308 through the software stack and receive a response as messages 312 in response to the API calls 308. The layers illustrated are representative in nature and not all software architectures have all layers. For example, some mobile or special purpose operating systems may not provide a frameworks/middleware 318, while others may provide such a layer. Other software architectures may include additional or different layers.

The operating system 302 may manage hardware resources and provide common services. The operating system 302 may include, for example, a kernel 322, services 324 and drivers 326. The kernel 322 may act as an abstraction layer between the hardware and the other software layers. For example, the kernel 322 may be responsible for memory management, processor management (e.g., scheduling), component management, networking, security settings, and so on. The services 324 may provide other common services for the other software layers. The drivers 326 are responsible for controlling or interfacing with the underlying hardware. For instance, the drivers 326 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 320 provide a common infrastructure that is used by the applications 316 and/or other components and/or layers. The libraries 320 provide functionality that allows other software components to perform tasks in an easier fashion than to interface directly with the underlying operating system 302 functionality (e.g., kernel 322, services 324 and/or drivers 326). The libraries 320 may include system libraries 344 (e.g., C standard library) that may provide functions such as memory allocation functions, string manipulation functions, mathematical functions, and the like. In addition, the libraries 320 may include API libraries 346 such as media libraries (e.g., libraries to support presentation and manipulation of various media format such as MPREG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 320 may also include a wide variety of other libraries 348 to provide many other APIs to the applications 316 and other software components/modules.

The frameworks/middleware 318 (also sometimes referred to as middleware) provide a higher-level common infrastructure that may be used by the applications 316 and/or other software components/modules. For example, the frameworks/middleware 318 may provide various graphic user interface (GUI) functions, high-level resource management, high-level location services, and so forth. The frameworks/middleware 318 may provide a broad spectrum of other APIs that may be utilized by the applications 316 and/or other software components/modules, some of which may be specific to a particular operating system or platform.

The applications 316 include built-in applications 338 and/or third-party applications 340. Examples of representative built-in applications 338 may include, but are not limited to, a contacts application, a browser application, a book reader application, a location application, a media application, a messaging application, and/or a game application. Third-party applications 340 may include any application developed using the ANDROID™ or IOS™ software development kit (SDK) by an entity other than the vendor of the particular platform and may be mobile software running on a mobile operating system such as IOS™, ANDROID™, WINDOWS® Phone, or other mobile operating systems. The third-party applications 340 may invoke the API calls 308 provided by the mobile operating system (such as operating system 302) to facilitate functionality described herein.

The applications 316 may use built-in operating system functions (e.g., kernel 322, services 324 and/or drivers 326), libraries 320, and frameworks/middleware 318 to create user interfaces to interact with users of the system. Alternatively, or additionally, in some systems, interactions with a user may occur through a presentation layer, such as presentation layer 314. In these systems, the application/component "logic" can be separated from the aspects of the application/component that interact with a user.

Some software architectures use virtual machines. In the example of FIG. 3, this is illustrated by a virtual machine 310. The virtual machine 310 creates a software environment where applications/components can execute as if they were executing on a hardware machine (such as the machine 400 of FIG. 4, for example). The virtual machine 310 is hosted by a host operating system (operating system (OS)

336 in FIG. 3) and typically, although not always, has a virtual machine monitor 360, which manages the operation of the virtual machine 310 as well as the interface with the host operating system (i.e., operating system 302). A software architecture executes within the virtual machine 310 such as an operating system (OS) 336, libraries 334, frameworks 332, applications 330 and/or presentation layer 328. These layers of software architecture executing within the virtual machine 310 can be the same as corresponding layers previously described or may be different.

Figure 4:
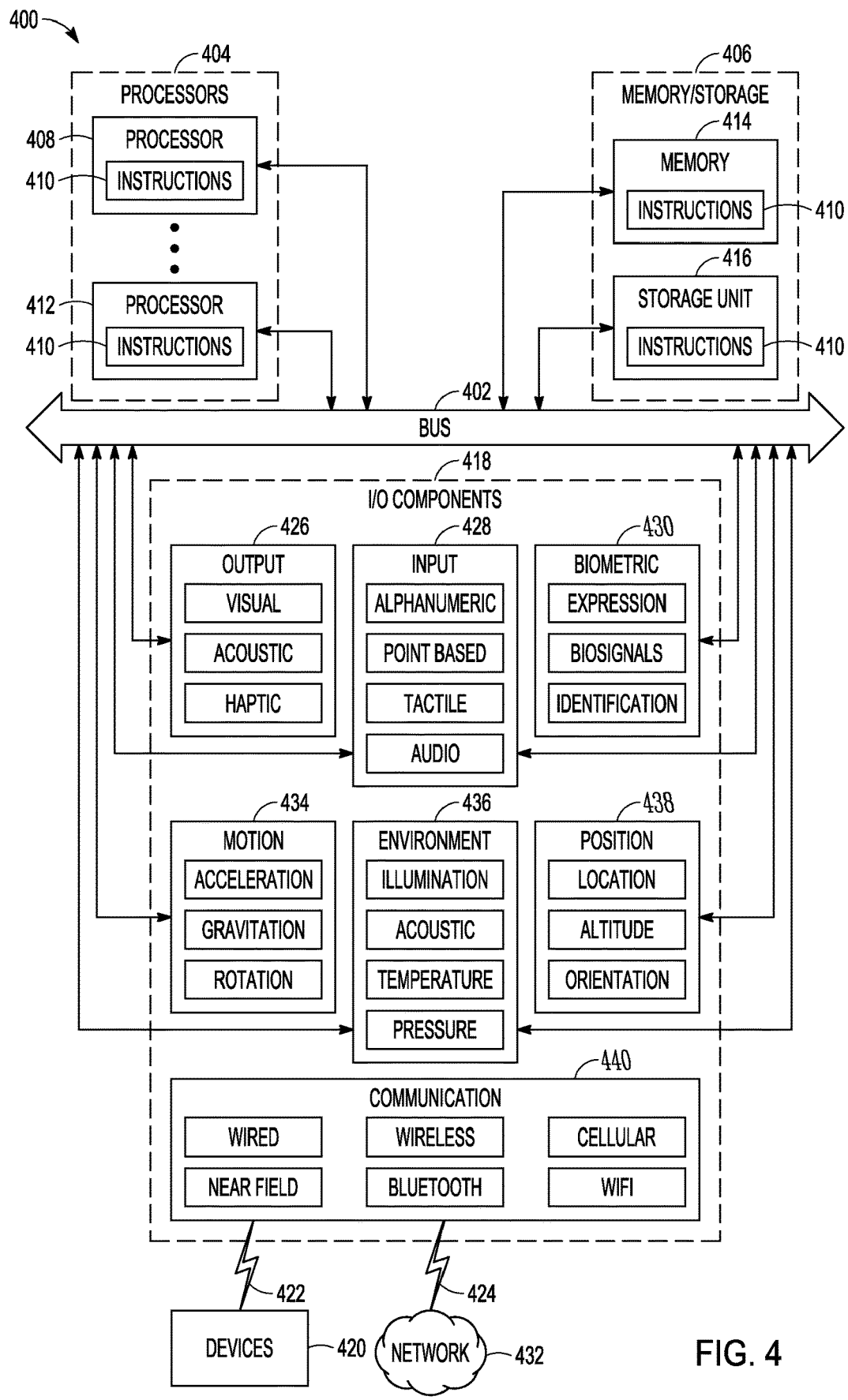
FIG. 4 is a block diagram illustrating components of a machine, according to some example embodiments, able to read instructions from a machine-readable medium (e.g., a machine-readable storage medium) and perform operations of any one or more of the methodologies discussed herein.

FIG. 4 is a block diagram illustrating components of a machine 400, according to some example embodiments, able to read instructions from a machine-readable medium (e.g., a machine-readable storage medium) and perform any one or more of the methodologies discussed herein. Specifically, FIG. 4 shows a diagrammatic representation of the machine 400 in the example form of a computer system, within which instructions 410 (e.g., software, a program, an application, an applet, an app, or other executable code) for causing the machine 400 to perform any one or more of the methodologies discussed herein may be executed. As such, the instructions 410 may be used to implement modules or components described herein. The instructions 410 transform the general, non-programmed machine into a particular machine programmed to carry out the described and illustrated functions in the manner described. In alternative embodiments, the machine 400 operates as a standalone device or may be coupled (e.g., networked) to other machines. In a networked deployment, the machine 400 may operate in the capacity of a server machine or a client machine in a server-client network environment, or as a peer machine in a peer-to-peer (or distributed) network environment. The machine 400 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 410, sequentially or otherwise, that specify actions to be taken by machine 400. Further, while only a single machine 400 is illustrated, the term "machine" shall also be taken to include a collection of machines that individually or jointly execute the instructions 410 to perform any one or more of the methodologies discussed herein.

The machine 400 may include processors 404, memory/storage 406, and I/O components 418, which may be configured to communicate with each other such as via a bus 402. The memory/storage 406 may include a memory 414, such as a main memory, or other memory storage, and a storage unit 416, both accessible to the processors 404 such as via the bus 402. The storage unit 416 and memory 414 store the instructions 410 embodying any one or more of the methodologies or functions described herein. The instructions 410 may also reside, completely or partially, within the memory 414, within the storage unit 416, within at least one of the processors 404 (e.g., within the processor's cache memory), or any suitable combination thereof, during execution thereof by the machine 400. Accordingly, the memory 414, the storage unit 416, and the memory of processors 404 are examples of machine-readable media.

The I/O components 418 may include a wide variety of components to receive input, provide output, produce output, transmit information, exchange information, capture measurements, and so on. The specific I/O components 418 that are included in a particular machine will depend on the type of machine. For example, portable machines such as mobile phones will likely include a touch input device or other such input mechanisms, while a headless server machine will likely not include such a touch input device. It will be appreciated that the I/O components 418 may include many other components that are not shown in FIG. 4. The I/O components 418 are grouped according to functionality merely for simplifying the following discussion and the grouping is in no way limiting. In various example embodiments, the I/O components 418 may include output components 426 and input components 428. The output components 426 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 428 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 418 may include biometric components 430, motion components 434, environment components 436, or position components 438 among a wide array of other components. For example, the biometric components 430 may include components to detect expressions (e.g., hand expressions, facial expressions, vocal expressions, body gestures, or eye tracking), measure bio signals (e.g., blood pressure, heart rate, body temperature, perspiration, or brain waves), identify a person (e.g., voice identification, retinal identification, facial identification, fingerprint identification, or electroencephalogram based identification), and the like. The motion components 434 may include acceleration sensor components (e.g., accelerometer), gravitation sensor components, rotation sensor components (e.g., gyroscope), and so forth. The environment components 436 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 438 may include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 418 may include communication components 440 operable to couple the machine 400 to a network 432 or devices 420 via coupling 422 and coupling 424 respectively. For example, the communication components 440 may include a network interface component or other suitable device to interface with the network 432. In further examples, communication components 440 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 420 may be another machine or any of a wide variety of peripheral devices (e.g., a peripheral device coupled via a Universal Serial Bus (USB)).

Moreover, the communication components 440 may detect identifiers or include components operable to detect identifiers. For example, the communication components 440 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 440, such as location via Internet Protocol (IP) geo-location, location via Wi-Fi® signal triangulation, location via detecting an NFC beacon signal that may indicate a particular location, and so forth.

As mentioned above, many PwP, due to the location of their residence or inability to travel, do not have access to a movement disorders specialist. Those who do have access typically see their neurologist no more than every six months. Standard therapy titration relies on a repeated process of clinical assessment at the office and patient interviews. For many patients, this infrequent interaction with their treating physician means that they endure suboptimal treatments for extended periods. For example, the battery of subjective tests referred to in the Background above include the following tests. For clarity of understanding, the description of these tests is based on the Part 3 Motor Test section of the UPDRS. Any copyright in this material sourced from the Movement Disorder Society is acknowledged. It will be apparent that the tests rely on a high degree of examiner subjectivity and are prone to human error.

3.1 SPEECH Instructions to examiner: Listen to the patient's free-flowing speech and engage in conversation if necessary. Suggested topics: ask about the patient's work, hobbies, exercise, or how s/he got to the doctor's office. Evaluate volume, modulation (prosody) and clarity, including slurring, palilalia (repetition of syllables) and tachyphemia (rapid speech, running syllables together).

| | |
|---|---|
| 0: Normal: | No speech problems. |
| 1: Slight: | Loss of modulation, diction or volume, but still all words easy to understand. |
| 2: Mild: | Loss of modulation, diction, or volume, with a few words unclear, but the overall sentences easy to follow. |
| 3: Moderate: | Speech is difficult to understand to the point that some, but not most, sentences are poorly understood. |
| 4: Severe: | Most speech is difficult to understand or unintelligible. |

3.2 FACIAL EXPRESSION Instructions to examiner: Observe the patient sitting at rest for 10 seconds, without talking and also while talking. Observe eye-blink frequency, masked facies or loss of facial expression, spontaneous smiling and parting of lips.

| | |
|---|---|
| 0: Normal: | Normal facial expression. |
| 1: Slight: | Minimal masked facies manifested only by decreased frequency of blinking. |
| 2: Mild: | In addition to decreased eye-blink frequency, Masked facies present in the lower face as well, namely fewer movements around the mouth, such as less spontaneous smiling, but lips not parted. |
| 3: Moderate: | Masked facies with lips parted some of the time when the mouth is at rest. |
| 4: Severe: | Masked facies with lips parted most of the time when the mouth is at rest. |

3.3 RIGIDITY Instructions to examiner: Rigidity is judged on slow passive movement of major joints with the patient in a relaxed position and the examiner manipulating the limbs and neck. First, test without an activation maneuver. Test and rate neck and each limb separately. For arms, test the wrist and elbow joints simultaneously. For legs, test the hip and knee joints simultaneously. If no rigidity is detected, use an activation maneuver such as tapping fingers, first opening/closing, or heel tapping in a limb not being tested. Explain to the patient to go as limp as possible as you test for rigidity.

| | |
|---|---|
| 0: Normal: | No rigidity. |
| 1: Slight: | Rigidity only detected with activation maneuver. |
| 2: Mild: | Rigidity detected without the activation maneuver, but full range of motion is easily achieved. |
| 3: Moderate: | Rigidity detected without the activation maneuver; full range of motion is achieved with effort. |
| 4: Severe: | Rigidity detected without the activation maneuver and full range of motion not achieved. |

3.4 FINGER TAPPING Instructions to examiner: Each hand is tested separately. Demonstrate the task, but do not continue to perform the task while the patient is being tested. Instruct the patient to tap the index finger on the thumb 10 times as quickly AND as big as possible. Rate each side separately, evaluating speed, amplitude, hesitations, halts and decrementing amplitude.

| | |
|---|---|
| 0: Normal: | No problems. |
| 1: Slight: | Any of the following: a) the regular rhythm is broken with one or two interruptions or hesitations of the tapping movement; b) slight slowing; c) the amplitude decrements near the end of the 10 taps. |
| 2: Mild: | Any of the following: a) 3 to 5 interruptions during tapping; b) mild slowing; c) the amplitude decrements midway in the 10-tap sequence. |
| 3: Moderate: | Any of the following: a) more than 5 interruptions during tapping or at least one longer arrest (freeze) in ongoing movement; b) moderate slowing; c) the amplitude decrements starting after the 1st tap. |
| 4: Severe: | Cannot or can only barely perform the task because of slowing, interruptions or decrements. |

3.5 HAND MOVEMENTS Instructions to examiner: Test each hand separately. Demonstrate the task, but do not continue to perform the task while the patient is being tested. Instruct the patient to make a tight first with the arm bent at the elbow so that the palm faces the examiner. Have the patient open the hand 10 times as fully AND as quickly as possible. If the patient fails to make a tight first or to open the hand fully, remind him/her to do so. Rate each side separately, evaluating speed, amplitude, hesitations, halts and decrementing amplitude.

| | |
|---|---|
| 0: Normal: | No problem. |
| 1: Slight: | Any of the following: a) the regular rhythm is broken with one or two interruptions or hesitations of the movement; b) slight slowing; c) the amplitude decrements near the end of the task. |
| 2: Mild: | Any of the following: a) 3 to 5 interruptions during the movements; b) mild slowing; c) the amplitude decrements midway in the task. |
| 3: Moderate: | Any of the following: a) more than 5 interruptions during the movement or at least one longer arrest (freeze) in ongoing movement; b) moderate slowing; c) the amplitude decrements starting after the 1st open-and-close sequence. |
| 4: Severe: | Cannot or can only barely perform the task because of slowing, interruptions or decrements. |

3.6 PRONATION-SUPINATION MOVEMENTS OF HANDS Instructions to examiner: Test each hand separately. Demonstrate the task, but do not continue to perform the task while the patient is being tested. Instruct the patient to extend the arm out in front of his/her body with the palms down; then to turn the palm up and down alternately 10 times as fast and as fully as possible. Rate each side separately, evaluating speed, amplitude, hesitations, halts and decrementing amplitude.

| | |
|---|---|
| 0: Normal: | No problems. |
| 1: Slight: | Any of the following: a) the regular rhythm is broken with one or two interruptions or hesitations of the movement; b) slight slowing; c) the amplitude decrements near the end of the sequence. |
| 2: Mild: | Any of the following: a) 3 to 5 interruptions during the movements; b) mild slowing; c) the amplitude decrements midway in the sequence. |
| 3: Moderate: | Any of the following: a) more than 5 interruptions during the movement or at least one longer arrest (freeze) in ongoing movement; b) moderate slowing c) the amplitude decrements starting after the 1st supination-pronation sequence. |
| 4: Severe: | Cannot or can only barely perform the task because of slowing, interruptions or decrements. |

3.7 TOE TAPPING Instructions to examiner: Have the patient sit in a straight-backed chair with arms, both feet on the floor. Test each foot separately. Demonstrate the task, but do not continue to perform the task while the patient is being tested. Instruct the patient to place the heel on the ground in a comfortable position and then tap the toes 10 times as big and as fast as possible. Rate each side separately, evaluating speed, amplitude, hesitations, halts and decrementing amplitude.

| | |
|---|---|
| 0: Normal: | No problem. |
| 1: Slight: | Any of the following: a) the regular rhythm is broken with one or two interruptions or hesitations of the tapping movement; b) slight slowing; c) amplitude decrements near the end of the ten taps. |
| 2: Mild: | Any of the following: a) 3 to 5 interruptions during the tapping movements; b) mild slowing; c) amplitude decrements midway in the task. |
| 3: Moderate: | Any of the following: a) more than 5 interruptions during the tapping movements or at least one longer arrest (freeze) in ongoing movement; b) moderate slowing; c) amplitude decrements after the first tap. |
| 4: Severe: | Cannot or can only barely perform the task because of slowing, interruptions or decrements. |

3.8 LEG AGILITY Instructions to examiner: Have the patient sit in a straight-backed chair with arms. The patient should have both feet comfortably on the floor. Test each leg separately. Demonstrate the task, but do not continue to perform the task while the patient is being tested. Instruct the patient to place the foot on the ground in a comfortable position and then raise and stomp the foot on the ground 10 times as high and as fast as possible. Rate each side separately, evaluating speed, amplitude, hesitations, halts and decrementing amplitude.

| | |
|---|---|
| 0: Normal: | No problems. |
| 1: Slight: | Any of the following: a) the regular rhythm is broken with one or two interruptions or hesitations of the movement; b) slight slowing; c) amplitude decrements near the end of the task. |
| 2: Mild: | Any of the following: a) 3 to 5 interruptions during the movements; b) mild slowness; c) amplitude decrements midway in the task. |
| 3: Moderate: | Any of the following: a) more than 5 interruptions during the movement or at least one longer arrest (freeze) in ongoing movement; b) moderate slowing in speed; c) amplitude decrements after the first tap. |
| 4: Severe: | Cannot or can only barely perform the task because of slowing, interruptions or decrements. |

3.9 ARISING FROM CHAIR Instructions to examiner: Have the patient sit in a straight-backed chair with arms, with both feet on the floor and sitting back in the chair (if the patient is not too short). Ask the patient to cross his/her arms across the chest and then to stand up. If the patient is not successful, repeat this attempt a maximum up to two more times. If still unsuccessful, allow the patient to move forward in the chair to arise with arms folded across the chest. Allow only one attempt in this situation. If unsuccessful, allow the patient to push off using his/her hands on the arms of the chair. Allow a maximum of three trials of pushing off. If still not successful, assist the patient to arise. After the patient stands up, observe the posture for item 3.13.

| | |
|---|---|
| 0: Normal: | No problems. Able to arise quickly without hesitation. |
| 1: Slight: | Arising is slower than normal; or may need more than one attempt; or may need to move forward in the chair to arise. No need to use the arms of the chair. |
| 2: Mild: | Pushes self up from arms of chair without difficulty. |
| 3: Moderate: | Needs to push off but tends to fall back; or may have to try more than one time using arms of chair but can get up without help. |
| 4: Severe: | Unable to arise without help. |

3.10 GAIT Instructions to examiner: Testing gait is best performed by having the patient walking away from and towards the examiner so that both right and left sides of the body can be easily observed simultaneously. The patient should walk at least 10 meters (30 feet), then turn around and return to the examiner. This item measures multiple behaviors: stride amplitude, stride speed, height of foot lift, heel strike during walking, turning, and arm swing, but not freezing. Assess also for "freezing of gait" (next item 3.11) while patient is walking. Observe posture for item 3.13.

| | |
|---|---|
| 0: Normal: | No problems. |
| 1: Slight: | Independent walking with minor gait impairment. |
| 2: Mild: | Independent walking but with substantial gait impairment. |
| 3: Moderate: | Requires an assistance device for safe walking (walking stick, walker) but not a person. |
| 4: Severe: | Cannot walk at all or only with another person's assistance. |

3.11 FREEZING OF GAIT Instructions to examiner: While assessing gait, also assess for the presence of any gait freezing episodes. Observe for start hesitation and stuttering movements especially when turning and reaching the end of the task. To the extent that safety permits, patients may NOT use sensory tricks during the assessment.

| | |
|---|---|
| 0: Normal: | No freezing. |
| 1: Slight: | Freezes on starting, turning or walking through doorway with a single halt during any of these events, but then continues smoothly without freezing during straight walking. |
| 2: Mild: | Freezes on starting, turning or walking through doorway with more than one halt during any of these activities, but continues smoothly without freezing during straight walking. |
| 3: Moderate: | Freezes once during straight walking. |
| 4: Severe: | Freezes multiple times during straight walking. |

3.12 POSTURAL STABILITY Instructions to examiner: The test examines the response to sudden body displacement produced by a quick, forceful pull on the shoulders while the patient is standing erect with eyes open and feet comfortably apart and parallel to each other. Test retropulsion. Stand behind the patient and instruct the patient on what is about to happen. Explain that s/he is allowed to take a step backwards to avoid falling. There should be a solid wall behind the examiner, at least 1-2 meters away to allow for the observation of the number of retropulsive steps. The first pull is an instructional demonstration and is purposely milder and not rated. The second time the shoulders are pulled briskly and forcefully towards the examiner with enough force to displace the center of gravity so that patient MUST take a step backwards. The examiner needs to be ready to catch the patient but must stand sufficiently back so as to allow enough room for the patient to take several steps to recover independently. Do not allow the patient to flex the body abnormally forward in anticipation of the pull. Observe for the number of steps backwards or falling. Up to and including two steps for recovery is considered normal, so abnormal ratings begin with three steps. If the patient fails to understand the test, the examiner can repeat the test so that the rating is based on an assessment that the examiner feels reflects the patient's limitations rather than misunderstanding or lack of preparedness. Observe standing posture for item 3.13.

| | |
|---|---|
| 0: Normal: | No problems: Recovers with one or two steps. |
| 1: Slight: | 3-5 steps, but subject recovers unaided. |
| 2: Mild: | More than 5 steps, but subject recovers unaided. |
| 3: Moderate: | Stands safely, but with absence of postural response; falls if not caught by examiner. |
| 4: Severe: | Very unstable, tends to lose balance spontaneously or with just a gentle pull on the shoulders. |

3.13 POSTURE Instructions to examiner: Posture is assessed with the patient standing erect after arising from a chair, during walking, and while being tested for postural reflexes. If you notice poor posture, tell the patient to stand up straight and see if the posture improves (see option 2 below). Rate the worst posture seen in these three observation points. Observe for flexion and side-to-side leaning.

| | |
|---|---|
| 0: Normal: | No problems. |
| 1: Slight: | Not quite erect, but posture could be normal for older person. |
| 2: Mild: | Definite flexion, scoliosis or leaning to one side, but patient can correct posture to normal posture when asked to do so. |
| 3: Moderate: | Stooped posture, scoliosis or leaning to one side that cannot be corrected volitionally to a normal posture by the patient. |
| 4: Severe: | Very unstable, tends to lose balance spontaneously or with just a gentle pull on the shoulders. |

3.14 GLOBAL SPONTANEITY OF MOVEMENT (BODY BRADYKINESIA) Instructions to examiner: This global rating combines all observations on slowness, hesitancy, and small amplitude and poverty of movement in general, including a reduction of gesturing and of crossing the legs. This assessment is based on the examiner's global impression after observing for spontaneous gestures while sitting, and the nature of arising and walking.

| | |
|---|---|
| 0: Normal: | No problems. |
| 1: Slight: | Slight global slowness and poverty of spontaneous movements. |
| 2: Mild: | Mild global slowness and poverty of spontaneous movements. |
| 3: Moderate: | Moderate global slowness and poverty of spontaneous movements. |
| 4: Severe: | Severe global slowness and poverty of spontaneous movements. |

3.15 POSTURAL TREMOR OF THE HANDS Instructions to examiner: All tremor, including re-emergent rest tremor, that is present in this posture is to be included in this rating. Rate each hand separately. Rate the highest amplitude seen. Instruct the patient to stretch the arms out in front of the body with palms down. The wrist should be straight, and the fingers comfortably separated so that they do not touch each other. Observe this posture for 10 seconds.

| | |
|---|---|
| 0: Normal: | No tremor. |
| 1: Slight: | Tremor is present but less than 1 cm in amplitude. |
| 2: Mild: | Tremor is at least 1 but less than 3 cm in amplitude. |
| 3: Moderate: | Tremor is at least 3 but less than 10 cm in amplitude. |
| 4: Severe: | Tremor is at least 10 cm in amplitude. |

3.16 KINETIC TREMOR OF THE HANDS Instructions to examiner: This is tested by the finger-to-nose maneuver. With the arm starting from the outstretched position, have the patient perform at least three finger-to-nose maneuvers with each hand reaching as far as possible to touch the examiner's finger. The finger-to-nose maneuver should be performed slowly enough not to hide any tremor that could occur with very fast arm movements. Repeat with the other hand, rating each hand separately. The tremor can be present throughout the movement or as the tremor reaches either target (nose or finger). Rate the highest amplitude seen.

| | |
|---|---|
| 0: Normal: | No tremor. |
| 1: Slight: | Tremor is present but less than 1 cm in amplitude. |
| 2: Mild: | Tremor is at least 1 but less than 3 cm in amplitude. |
| 3: Moderate: | Tremor is at least 3 but less than 10 cm in amplitude. |
| 4: Severe: | Tremor is at least 10 cm in amplitude. |

3.17 REST TREMOR AMPLITUDE Instructions to examiner: This and the next item have been placed purposefully at the end of the examination to allow the rater to gather observations on rest tremor that may appear at any time during the exam, including when quietly sitting, during walking and during activities when some body parts are moving but others are at rest. Score the maximum amplitude that is seen at any time as the final score. Rate only the amplitude and not the persistence or the intermittency of the tremor.

As part of this rating, the patient should sit quietly in a chair with the hands placed on the arms of the chair (not in the lap) and the feet comfortably supported on the floor for 10 seconds with no other directives. Rest tremor is assessed separately for all four limbs and also for the lip/jaw. Rate only the maximum amplitude that is seen at any time as the final rating.

Extremity Ratings

| | |
|---|---|
| 0: Normal: | No tremor. |
| 1: Slight: | <1 cm in maximal amplitude. |
| 2: Mild: | >1 cm but <3 cm in maximal amplitude. |
| 3: Moderate: | 3-10 cm in maximal amplitude. |
| 4: Severe: | >10 cm in maximal amplitude. |

Lip/Jaw Ratings

| | |
|---|---|
| 0: Normal: | No tremor. |
| 1: Slight: | <1 cm in maximal amplitude. |
| 2: Mild: | >1 cm but <2 cm in maximal amplitude. |
| 3: Moderate: | >2 cm but <3 cm in maximal amplitude. |
| 4: Severe: | >3 cm in maximal amplitude. |

3.18 CONSTANCY OF REST TREMOR Instructions to examiner: This item receives one rating for all rest tremor and focuses on the constancy of rest tremor during the examination period when different body parts are variously at rest. It is rated purposefully at the end of the examination so that several minutes of information can be coalesced into the rating.

| | |
|---|---|
| 0: Normal: | No tremor. |
| 1: Slight: | Tremor at rest is present <25% of the entire examination period. |
| 2: Mild: | Tremor at rest is present 26-50% of the entire examination period. |
| 3: Moderate: | Tremor at rest is present 51-75% of the entire examination period. |
| 4: Severe: | Tremor at rest is present >75% of the entire examination period. |

This disclosure provides a facilitated method using improved technology to expedite and simplify a quantitative evaluation of body movement disorder and different titration regimens. Enabling multiple quantitative evaluations to be performed by the patient at home may save the physician time and improve patient outcomes, thus making the process more efficient. In some examples, at least sixteen of the eighteen Part 3 motor tests listed may be suitable for virtual analysis using the methods described herein. Motor tests requiring significant rigidity and postural stability may require increased physical interaction of the clinician with the patient and are not a good subject for automated testing accordingly.

Complex medication regimens, intraday symptom fluctuations and cognitive issues make managing the disease a challenge for PwP and their caregivers. Current objective diagnostic sensors and other tools have cost and logistical barriers. They are marketed to healthcare professionals and researchers, not PwP who are left to manage their disease with inadequate tools.

The technical improvements and functionality disclosed in this application add significant objectivity to standard outcome measures that will help advance treatment plans for the hard-to-measure movement disorders. The evolution and integration of technology and medicine described herein allows movement disorder neurologists, physicians and nurses to have very minimal, if any, interrater variability (IRV) when using the UPDRS. The present technology enables pharmaceutical companies to gather more consistent and accurate data by eliminating the subjective component in the rating of the UPDRS. This objective standard can help to show that certain drugs are efficacious across large study populations and can potentially save thousands if not millions of dollars in the process of getting drugs FDA approved in clinical trials. Primary investigators can employ a nurse or research coordinator to do the majority of the UPDRS assessment with confidence that the rating will be the same as if the physician did it.

The present disclosure also significantly decreases the time it takes to complete the UPDRS in the research and in clinical practice. Since most neurologists do not routinely use the UPDRS in clinical practice the present application would increase the numbers of those that do. The present disclosure seeks to change the way Parkinson's disease and other movement disorder patients are evaluated by making this faster and more accurate, and by eliminating IRV, human error and subjective scoring. Its application can extend to treatment for diseases such as Essential Tremor, Chorea, Tardive Dyskinesia (TD) and Blepharospasm (BS) will also improve with more precise and objective measures of disease state and rate of change.

Technical solutions of the present disclosure include standardization in the measurement of abnormal movements. Variability in doctor scores is a reality. The present disclosure seeks to provide the same score, for the same patient (subject), regardless of a doctor or examiner conducting a test. Embodiments of the present disclosure substantially remove subjectivity and human error. The improved technology described herein facilitates access to democratized global health care, an objective measurement of symptoms and the effects of medication on symptoms, and a more reliable and accurate view of a disease progression over time.

As a value proposition, the systems and methods described herein allow symptoms to be conveniently evaluated at home throughout the day. A more complete picture of symptoms is provided. While the present systems and methods may not replace a physician, they save time and money and substantially eliminate human error and subjectivity. In some examples, use of the disclosed system is billable to medical aid societies (e.g. Medicare) as part of a neural examination. The time taken to evaluate a patient is minimized, and test data can be visually validated with a video and photo summary in a test report. In some examples, a nurse may perform a movement disorder test which qualifies as a neural exam and is billable to Medicare. A doctor may perform further parts of the test and copy and paste his or her results into a composite test report.

Global clinical trials using the systems and methods described herein have eliminate clinical trial site variability and error rates and allow the diversified study of different demographic populations globally.

As the inevitable advance in telemedicine proceeds, the present systems and methods provide access to movement disorder testing globally, for example in assisting underserved regions. The establishment of global standards is facilitated while enabling clinical trial diversity. The objectivity of the results adds a validation layer and substantially eliminates human error.

Movement disorder diseases that may be treated include chorea, Tardive Dyskinesia (TD), Blepharospasm (BS), essential tremor, PD, and Dyskinesia. In relation to Dyskinesia specifically, alleviation of movement in the arms and neck may alleviate movement in a subject's face. Some examples employ different observation angles for dyskinesia, for looking down at the top of the head.

Measuring Movement Disorder Symptoms

In some examples, reference objects and computer vision techniques are used to determine the physical scale and the degree of movement of objects in the video. Once the scale of the subject, body part or facial landmark has been determined it is possible to track and measure movement of the body and its various objects from frame to frame. For instance, a subject may be six feet tall and based on that information an accurate scale of body parts and movement in relation to them can be developed.

Facial Recognition

Figure 5B:
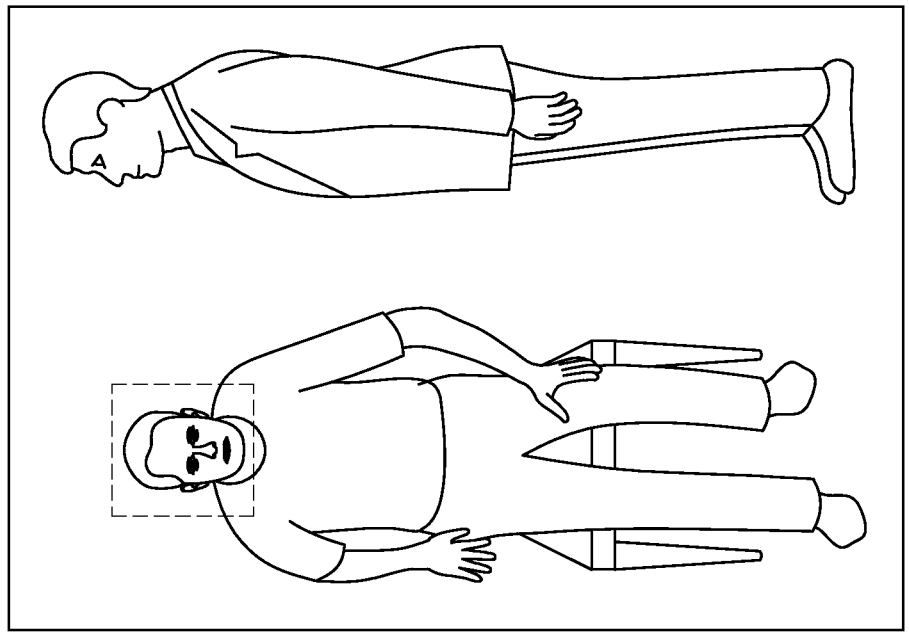
FIGS. 5A-5B is a schematic view of facial recognition in an Arising-From-Chair test, according to an example embodiment.
Figure 5A:
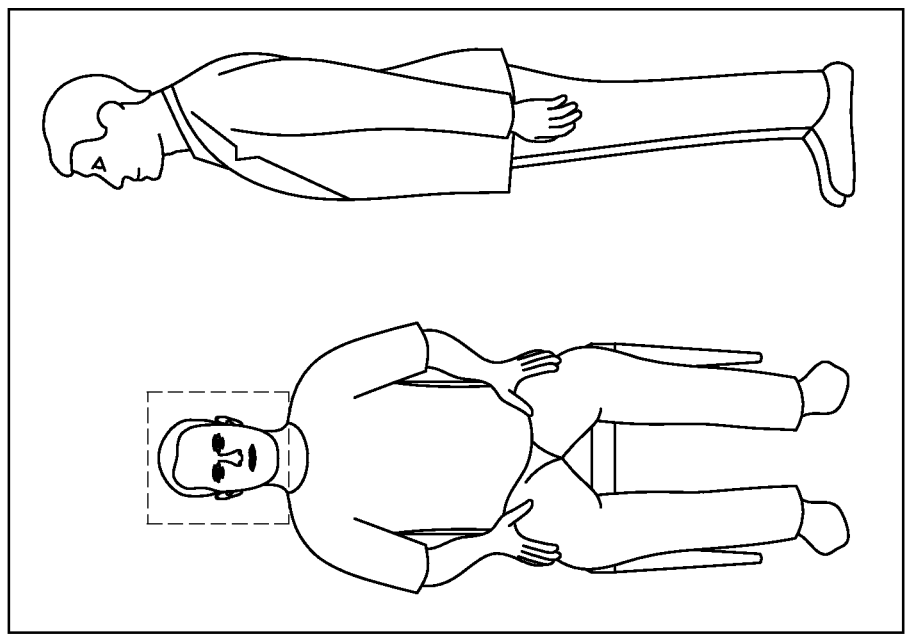

Some examples employ and object detection tool. An example tool may include an object detection framework for detecting objects in real time. It is used primarily to detect faces. An example algorithm has four stages and works be analyzing pixels within rectangular areas. All human faces share similar properties with respect location of eyes, nose and mouth. In some examples, the algorithm identifies facial regions such as the bridge of the nose which has a bright vertical area where the bridge of the nose reflects light. With reference to FIGS. 5A-5B, once a face is isolated it can be tracked and measured to determine how quickly the subject stands up and completes testing procedures.

Hand Gesture Recognition

Figure 6B:
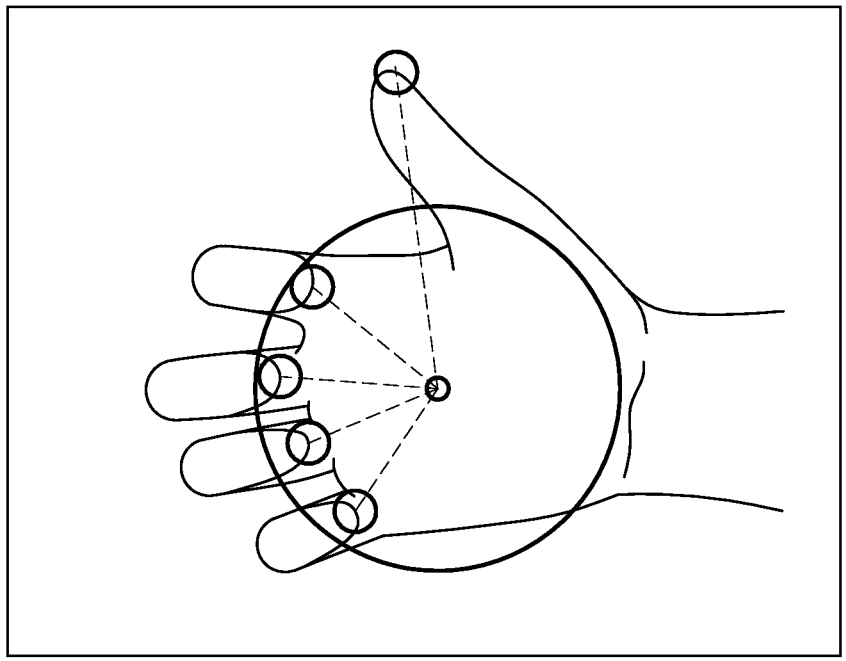
FIGS. 6A-6B is a schematic view of finger tracking in a Finger Tapping test, according to an example embodiment.
Figure 6A:
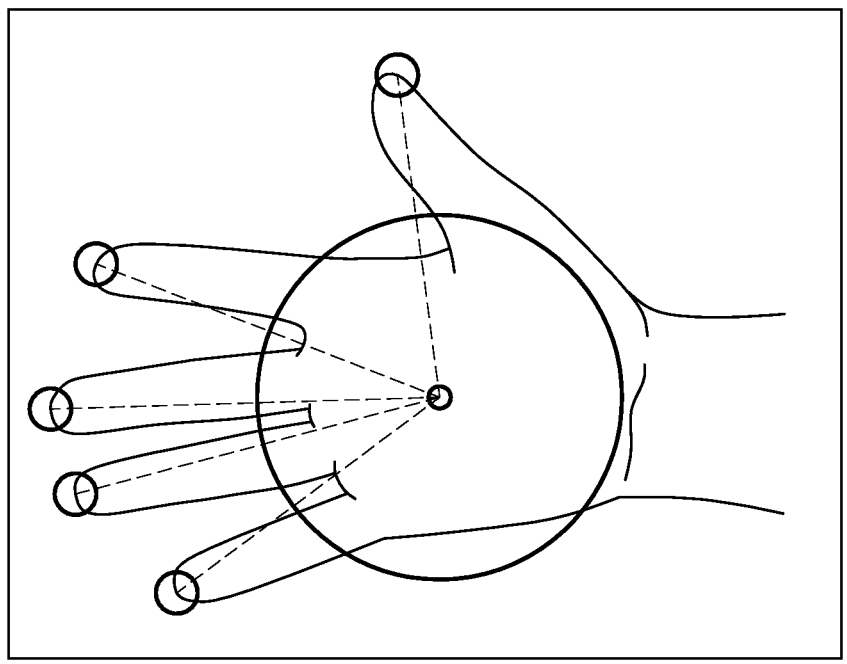

In some examples, an image isolation tool may be used to isolate the hand image from the background of the video based, for example, on skin color and the contrast from the background. The video background and certain contours of the hand and fingers may be extracted using an extraction function. Finger tips are convex points and the area in between the base of the fingers are defect points. With reference to FIGS. 6A-6B, once the tips of the fingers have been detected it is possible to track and measure finger tapping speed, amplitude, hesitations, halts and decrementing amplitude objectively.

Facial Landmark Detection

Figure 7:
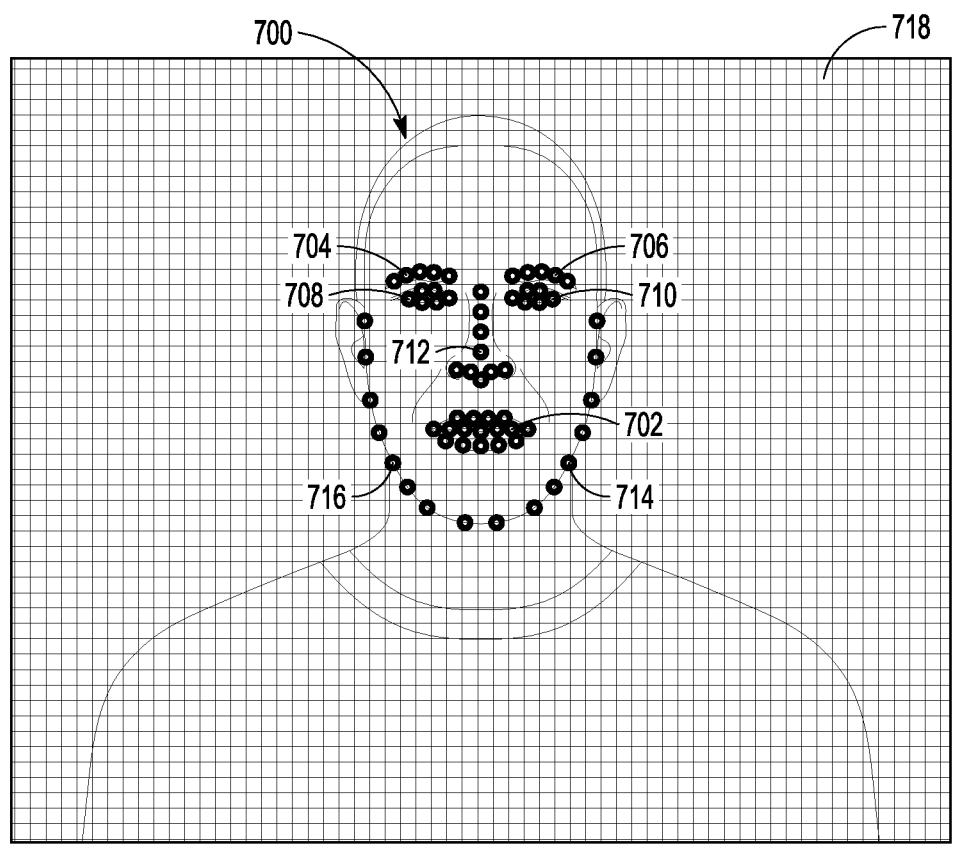
FIG. 7 is a schematic view of detected facial landmarks and a measurement grid displayed at face depth, according to an example embodiment.

In some examples, video recorded with a single RGB camera is run through a series of algorithms to determine the location of facial features and provide a scale grid used to measure the movement of the subject. A feature location tool may be used to locate facial features and plot a series of markers that map to specific facial regions. With reference to FIG. 7, facial regions of a subject 700 can be detected and may include regions such as the mouth 702, the right eyebrow 704, the left eyebrow 706, the right eye 708, the left eye 710, the nose 712, and the jaw 714. Each region may be defined by a set of points 716.

Measurement Grid

In some examples, computer vision and augmented reality techniques are used to identify and measure objects in a video stream. Once a measurement scale has been determined, a virtual grid 718 is placed at front-of-face depth. The virtual grid is used to determine the objective measure of body movement during the video sequence. In some examples, each grid square represents 1 cm of distance laterally at the face.

De-Identification

Patient and study subject identities can be masked and only markers representing the body parts being measured are displayed. This privacy element has the potential to aid in clinical trial recruitment.

Summary Image Snapshot

Individual body part key points are tracked over the course of the video and the location of each is stored for analysis. At the end of the process an image is created which summarizes the movement of each key point with color coded lines. This image is a visual representation of the severity of movement and allows for a fast and simple understanding of motor symptoms.

Facial Landmark Overlays

Figure 8:
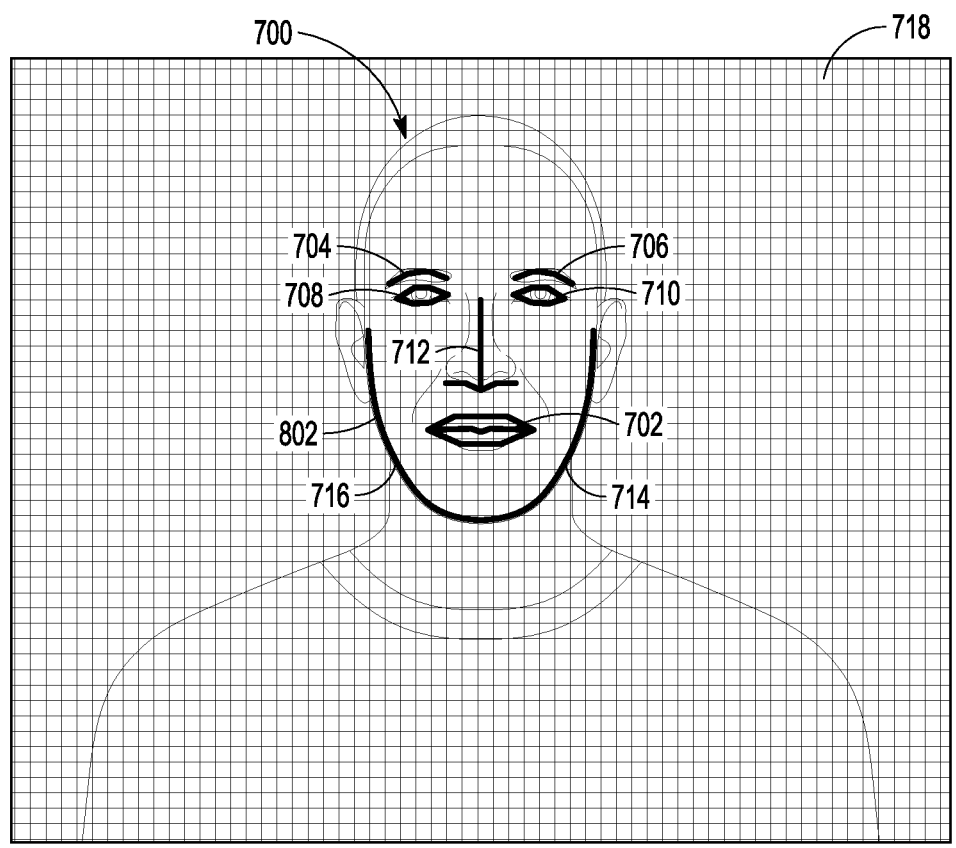
FIG. 8 is a schematic view of a location and proportion of facial landmarks, according to an example embodiment.

With reference to FIG. 8, facial landmarks, such as one or more of the regions 702-714 shown in FIG. 7, are highlighted visually by connecting the points 716 in each region to define a respective line 802 for each region 702-714. These facial feature outlines 802 are used in some examples to visually identify and track each facial landmark independently.

Tracking Movement

Figure 9:
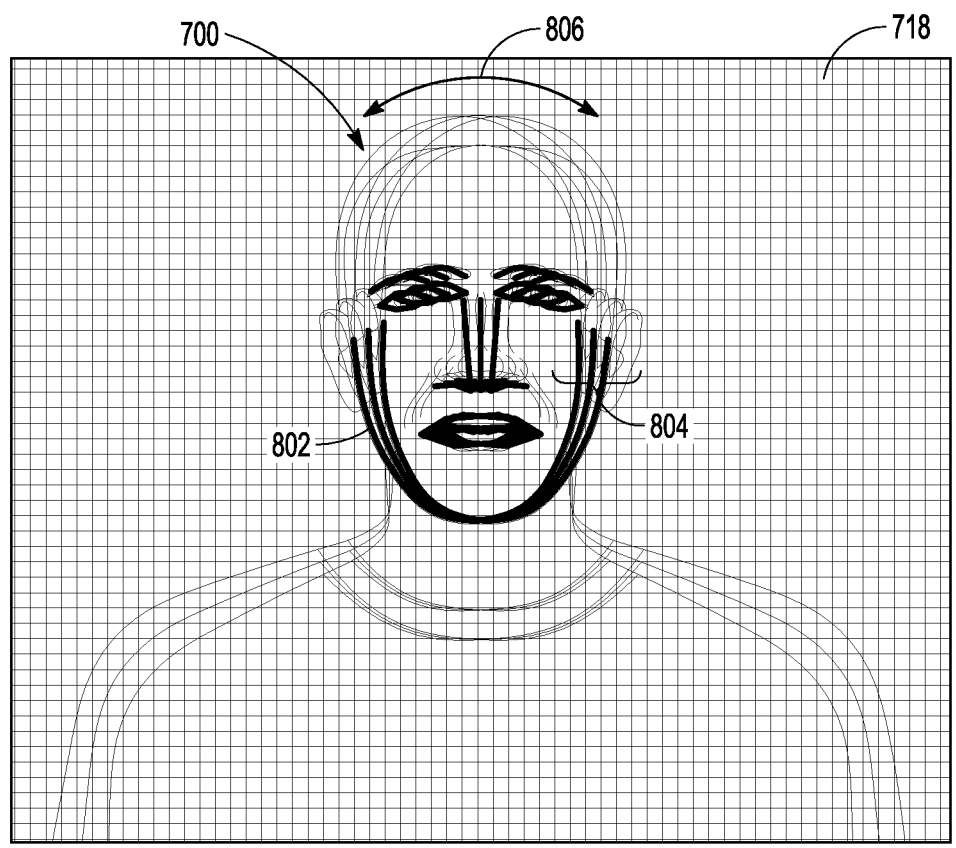
FIG. 9 is a schematic view of a facial landmark movement amplitude over time validated with video frame grabs, according to an example embodiment.
Figure 10:
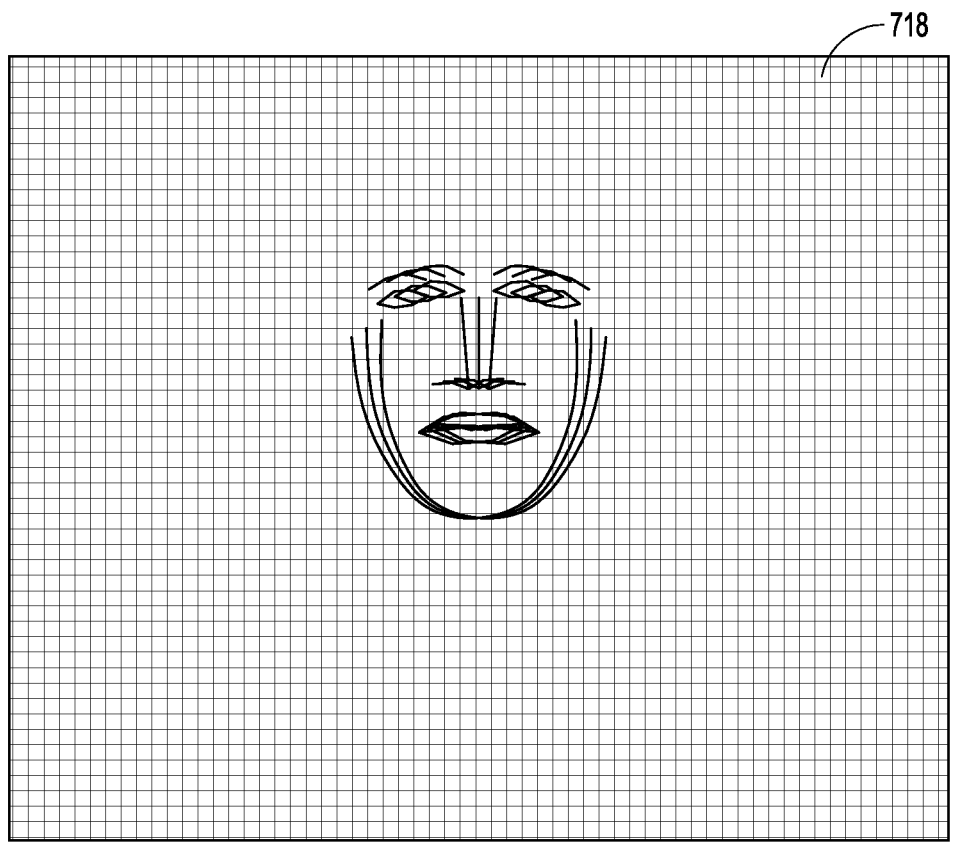
FIG. 10 is a schematic view of a facial landmark image amplitude taken from a movement analysis displayed with a grid and without the subject's facial image, according to an example embodiment.

With reference to FIG. 9, in some examples various techniques are employed to validate the objective measures of movement in relation to the grid. In some examples, the point of a visual validation is to provide a quick and intuitive summary of movement that corroborates other independent data. Summarizing the movement in a manner that supports the current measurement by observation will improve understanding and adoption of this method. A set 804 of lines 802 for each facial feature outline may be generated based on the movement of the subject 700, for example as shown at 806. With reference to FIG. 10, for privacy or other reasons, the facial landmarks can be separated from the background images of the subject 700. This may allow for a more focused summary of movement in relation to the grid.

Facial Landmark Behavior Detection

Figure 11:
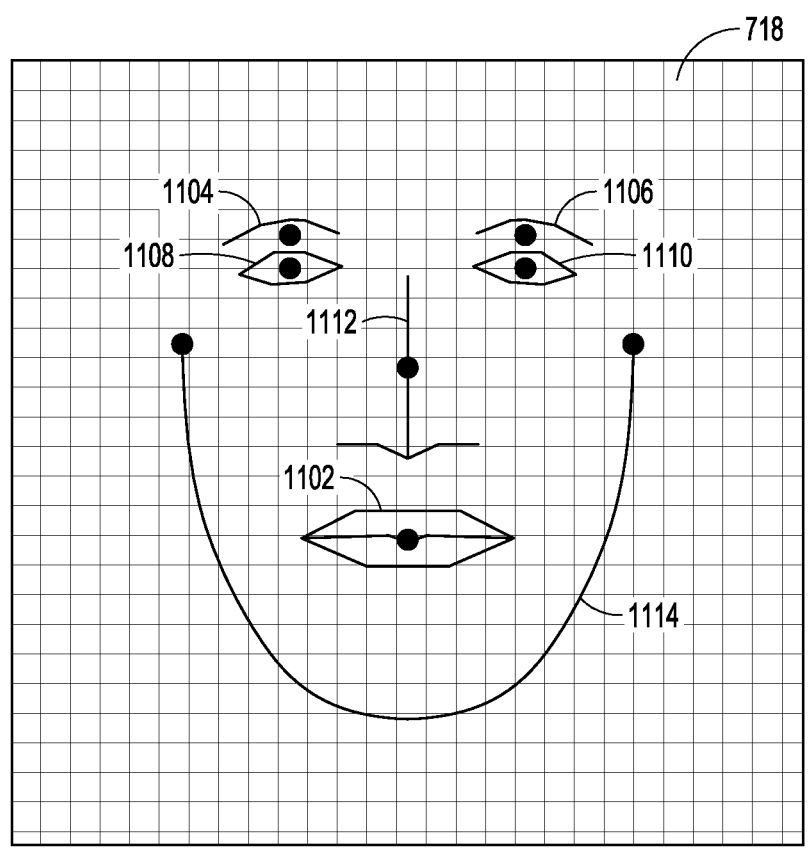
FIG. 11 is a schematic view of subject facial landmarks with eyes open, according to an example embodiment.
Figure 12:
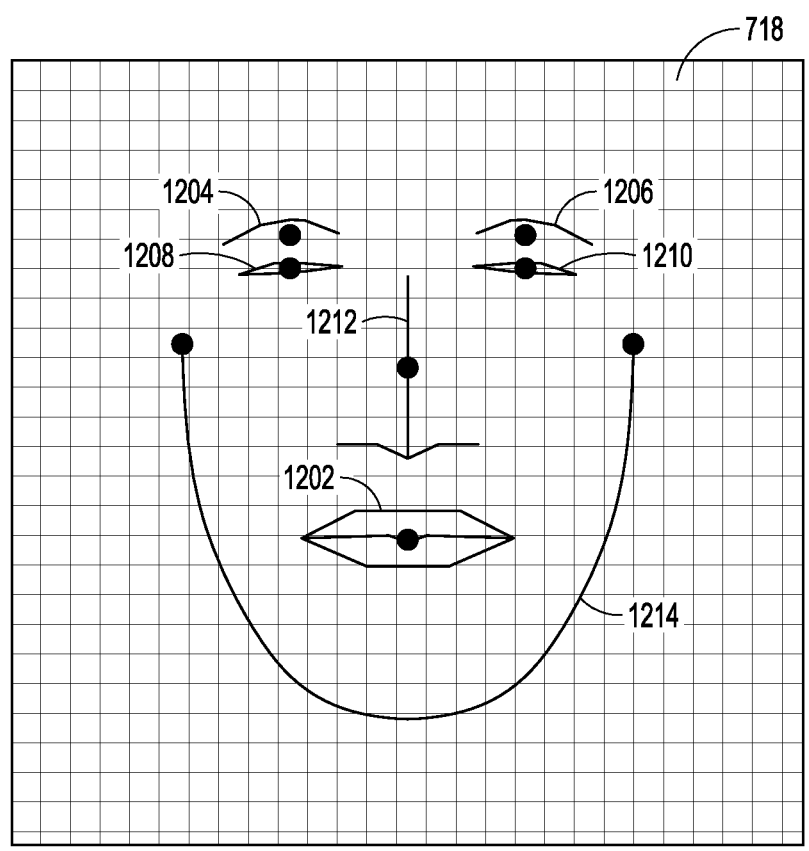
FIG. 12 is a schematic view of subject facial landmarks with eyes closed, according to an example embodiment.
Figure 13:
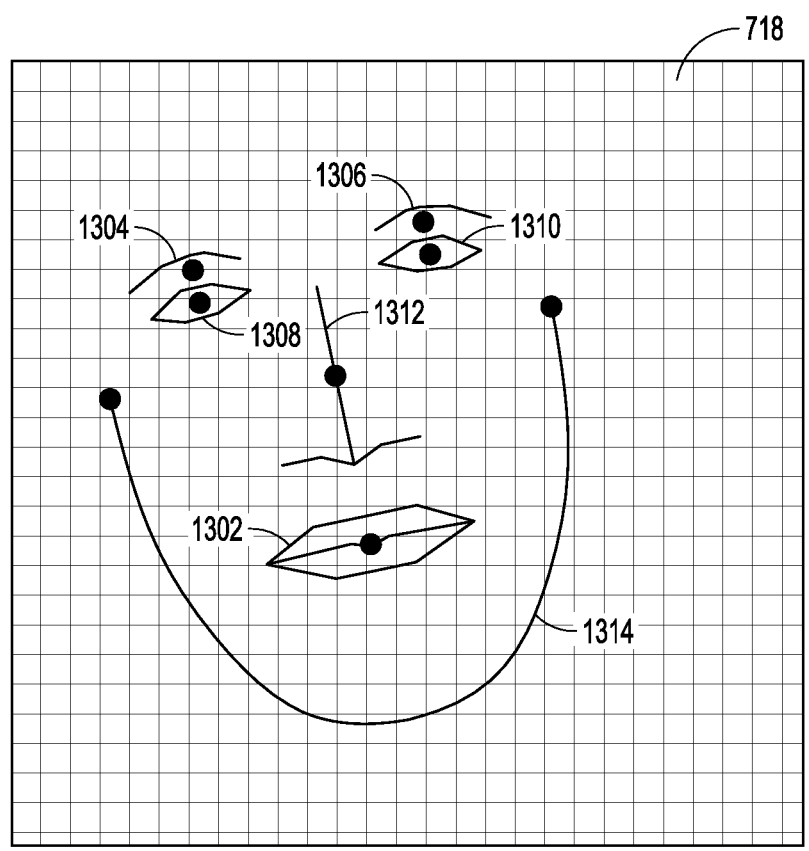
FIG. 13 is a schematic view of subject facial landmarks with head tilted, according to an example embodiment.

With reference to FIGS. 11, 12, and 13, because the facial features 1102-1114, 1202-1214, and 1302-1314 can be identified and tracked in relation to the grid 718, as a group and individually and by themselves, subject behaviors such as opening a mouth, raising an eyebrow, tilting a head and closing an eye can be detected and measured with objective precision. Some examples can include determining how many times the subject blinked or closed an eye, or how many milliseconds was an eye closed. Other examples may determine whether the duration and severity of the closed eye increased over time. These aspects and others can be measured and reported objectively thereby saving time and improving insight for scarce medical specialists, measuring the impact of medications objectively and without friction and improving outcomes for patients who are empowered to understand their condition by measuring their own symptoms.

Measuring Facial Landmark Amplitude

Figure 14:
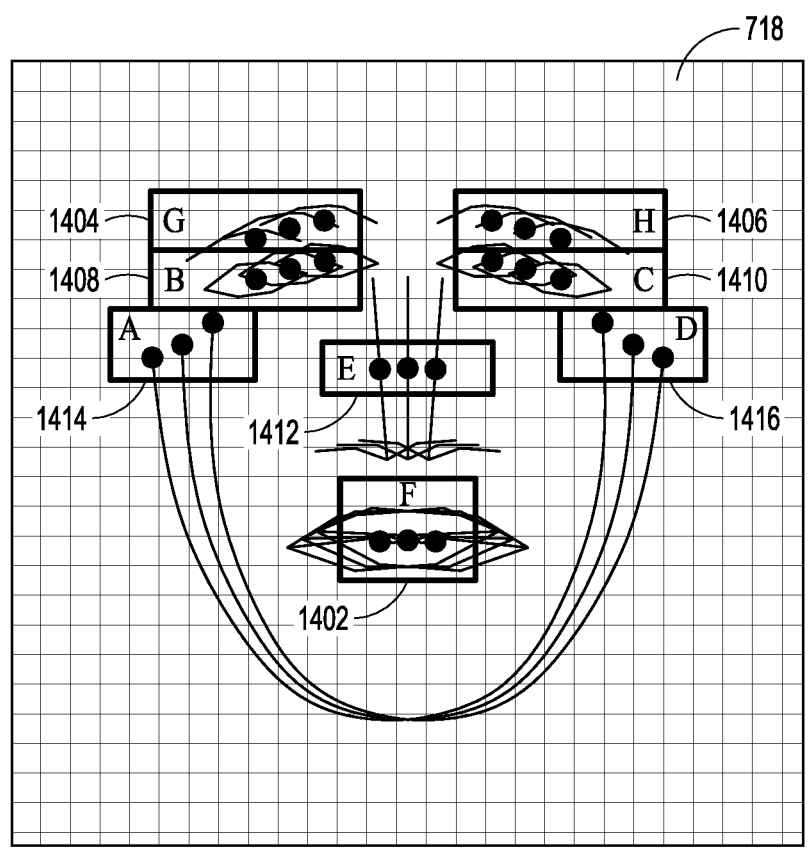
FIG. 14 is a schematic view of subject facial landmark amplitude over time, according to an example embodiment.

With reference to FIG. 14, in some examples the coordinates of facial features such as eyes, nose, mouth, eyebrows, top of left jawline and top of right jawline are measured for vertical, horizontal amplitude and velocity of movement. The features are labeled in the view as noted in the table below.

| Region | Region Code | Vertical | Horizontal |
|---|---|---|---|
| Right Eye | B (1408) | 2.8 cm | 8.5 cm |
| Left Eye | C (1410) | 2.3 cm | 4.1 cm |
| Nose | E (1412) | 2.8 cm | 8.1 cm |
| Mouth | F (1402) | 2.0 cm | 5.4 cm |
| Right Jawline | A (1414) | 3.0 cm | 5.0 cm |
| Left Jawline | D (1416) | 2.7 cm | 5.9 cm |
| Right Eyebrow | G (1404) | 2.4 cm | 8.4 cm |
| Left Eyebrow | H (1406) | 2.2 cm | 4.2 cm |

This movement information is directly relevant for measuring the effect of medications on movement disorders such as dyskinesias where symptoms may fluctuate intra-day and the subject may not even realize they are experiencing movement at all.

Measuring Body Part Amplitude

Figure 15:
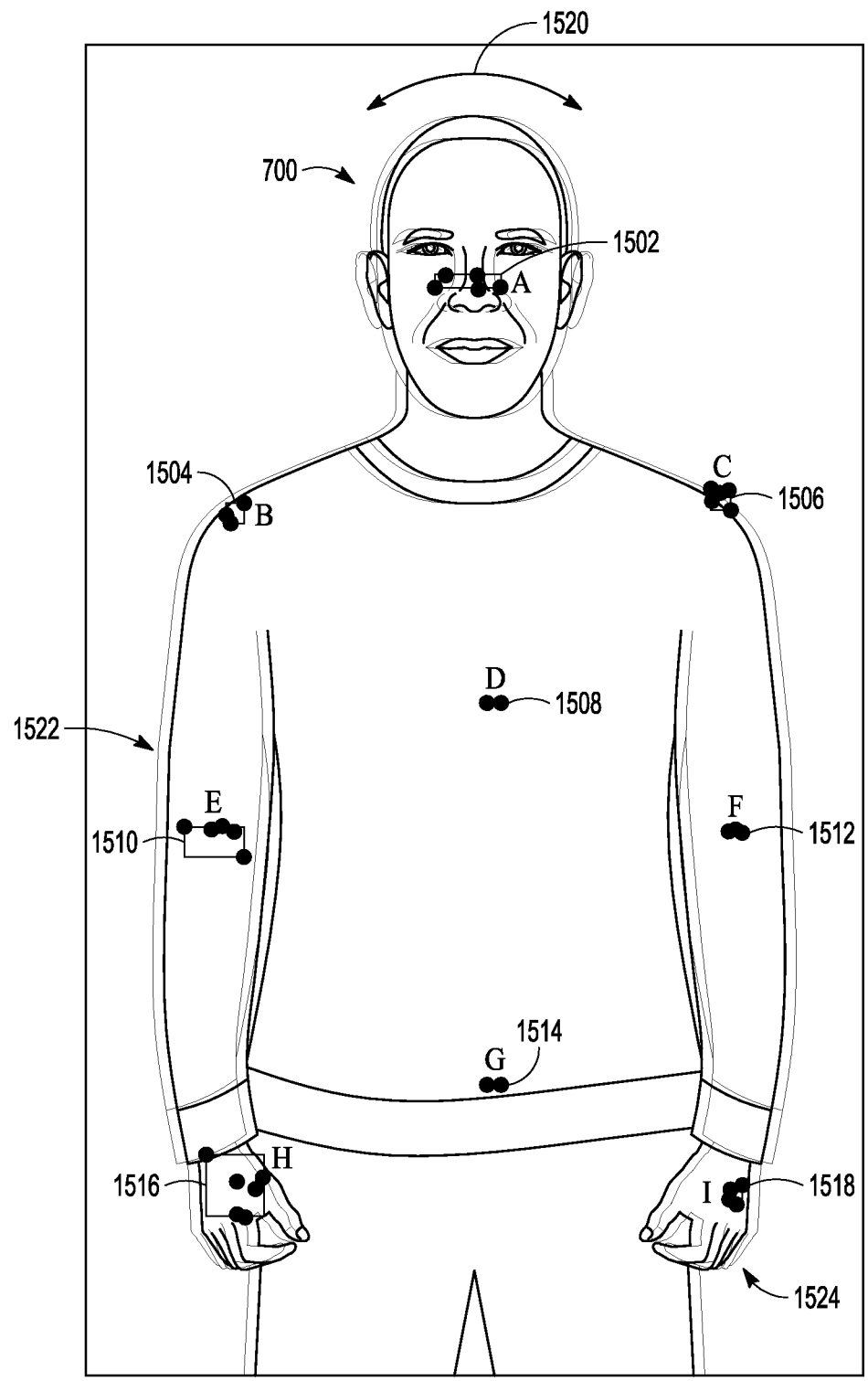
FIG. 15 is a schematic view of body part amplitude, according to an example embodiment.
Figure 16:
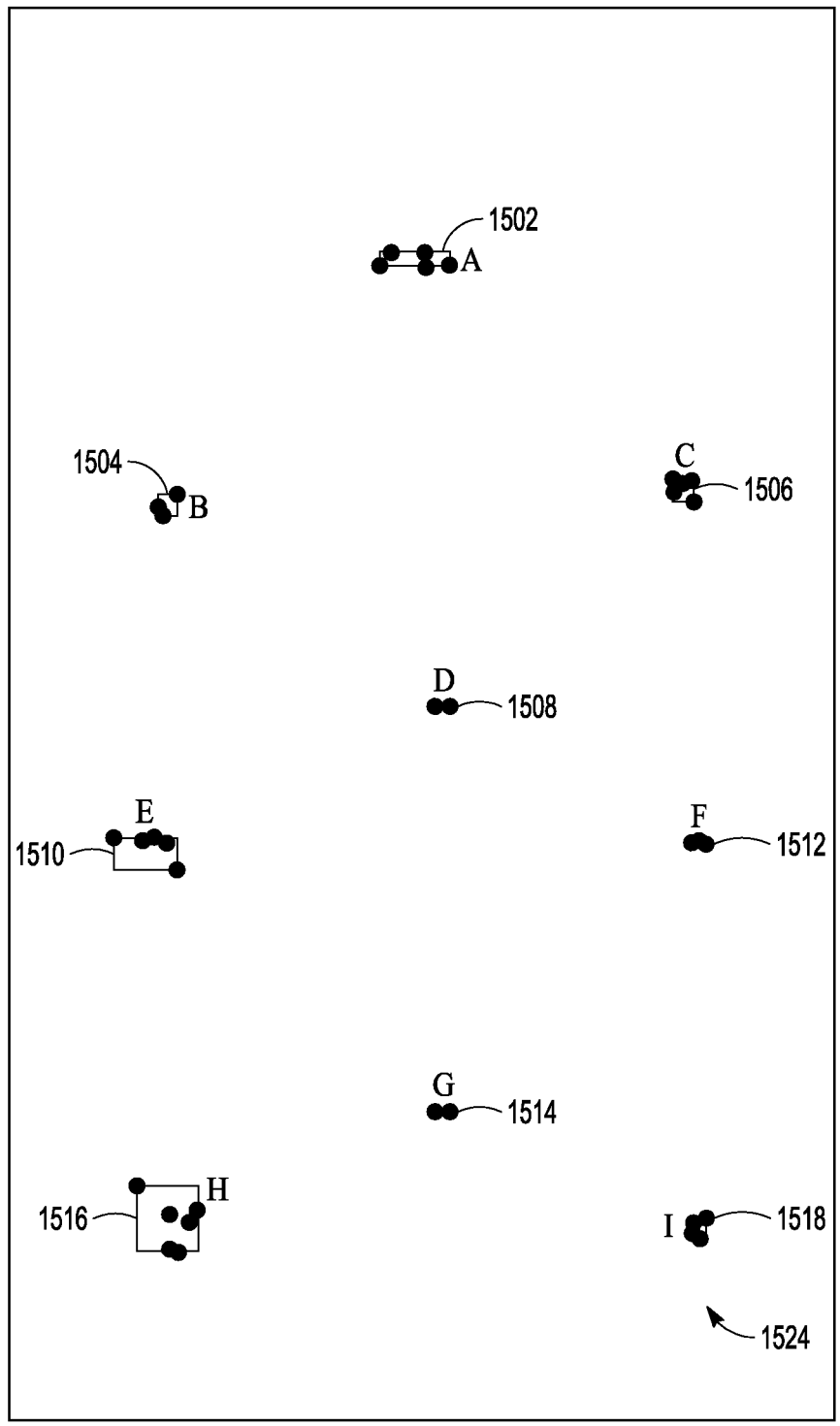
FIG. 16 is a schematic view of body part amplitude in a privacy mode (subject images removed), according to an example embodiment.

In some examples, with reference to FIGS. 15 and 16, the coordinates of the head, shoulders, chest, waist, elbows and hands of a subject 700 are measured for vertical, horizontal amplitude and velocity of movement. Example directions of reciprocating or shaky head, elbow and hand movements are indicated at 1520, 1522, and 1524, respectively.

| Region | Region Code | Vertical | Horizontal |
|---|---|---|---|
| Head | A (1502) | 1.3 cm | 6.2 cm |
| Right Shoulder | B (1504) | 1.9 cm | 1.4 cm |
| Left Shoulder | C (1506) | 2.2 cm | 1.8 cm |
| Chest | D (1508) | 0.2 cm | 1.4 cm |
| Right Elbow | E (1510) | 2.7 cm | 5.5 cm |
| Left Elbow | F (1512) | 0.3 cm | 1.2 cm |
| Right Hand | H (1516) | 2.4 cm | 8.4 cm |
| Left Hand | I (1518) | 5.8 cm | 5.4 cm |

In further examples of measuring movement disorder symptoms, deep learning pose estimation algorithms are used for vision-based assessment of parkinsonism and levodopa-induced dyskinesia (LID). A deep learning pose estimation method may be used to extract movement trajectories from videos of PD assessments. Features of the movement trajectories can be used to detect and estimate the severity of parkinsonism.

Figure 17A:
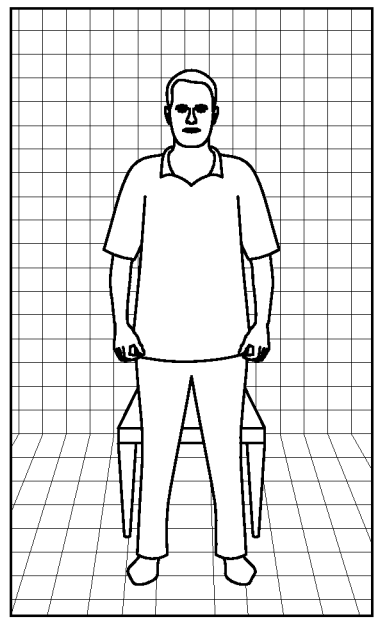
FIGS. 17A-17D represent certain observations, operations and graphed results in an example image processing of a video to measure and visualize a level of a subject's dyskinesia, according to example embodiments.
Figure 17B:
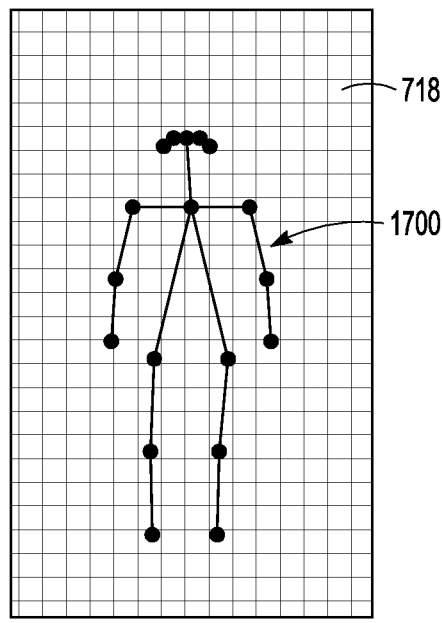
Figure 17C:
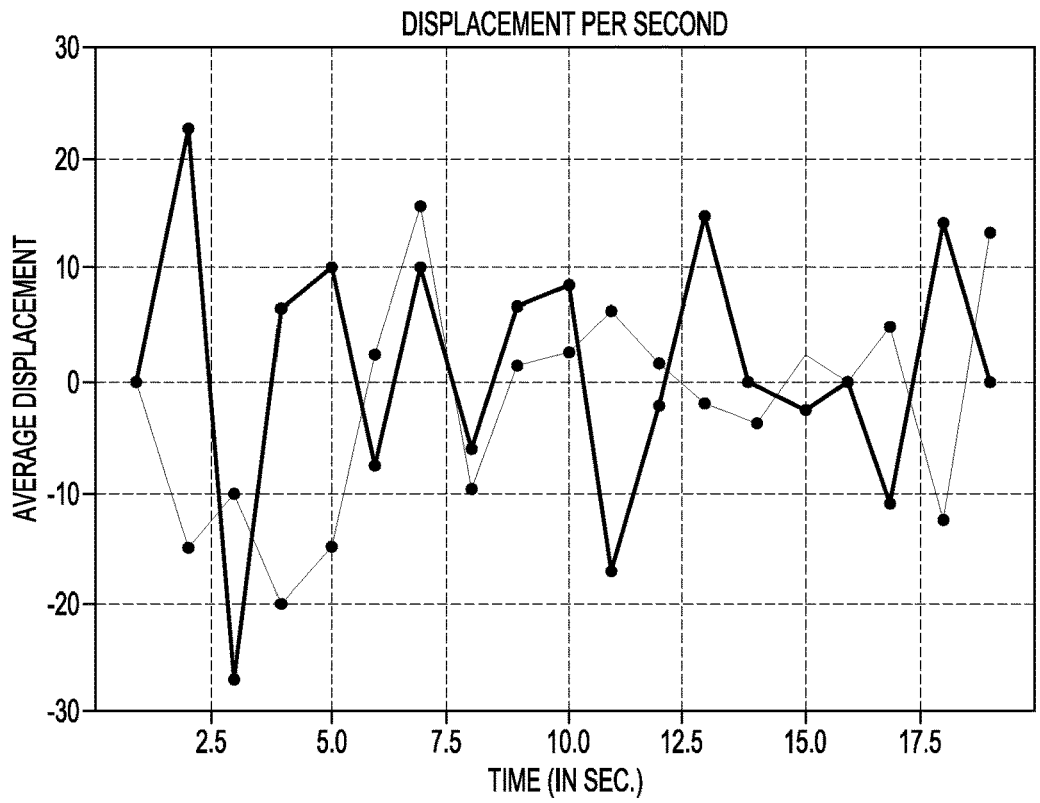
Figure 17D:
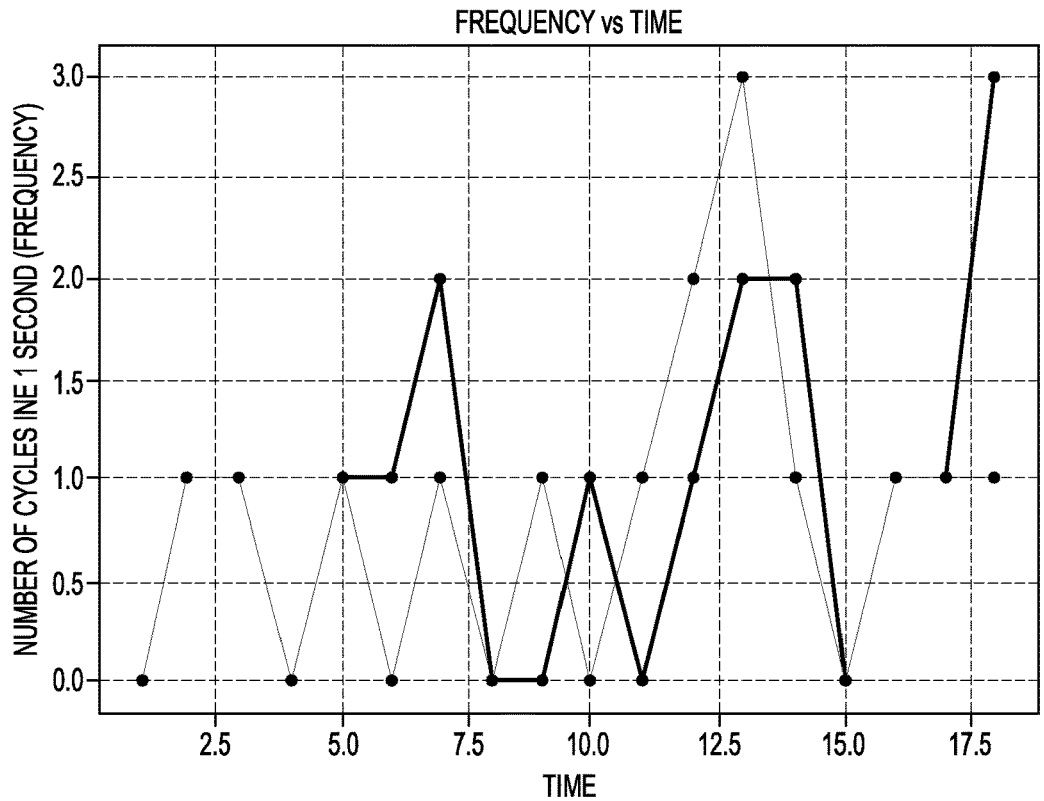

FIGS. 17A-17D represent operations in an example image processing of a video to measure and visualize the level of a subject's dyskinesia. FIG. 17A depicts an image of a subject (patient) undergoing a PD assessment. In FIG. 17B, a "skeleton extraction" operation is performed. A complete skeleton of the patient may be extracted. In some examples, a skeleton is extracted using extraction tool. In some examples, the extraction tool is a real-time multi-person system to jointly detect human body, hand, and facial key points (in total 135 key points) on single images. In some examples, the 135 key points comprise the following: 15, 18, or 25-key point body or foot estimations; 2 times 21-key point hand key point estimation (two hands), and 70-key point face key point estimation. Dyskinesial movement of a skeleton which is representative of Dyskinesial movement of the patient may be observed objectively (without intervention of a human observer) using the extraction tool with reference to a grid 718. Example results of the assessment may be graphed as shown in FIGS. 17C-17D.

Figure 18:
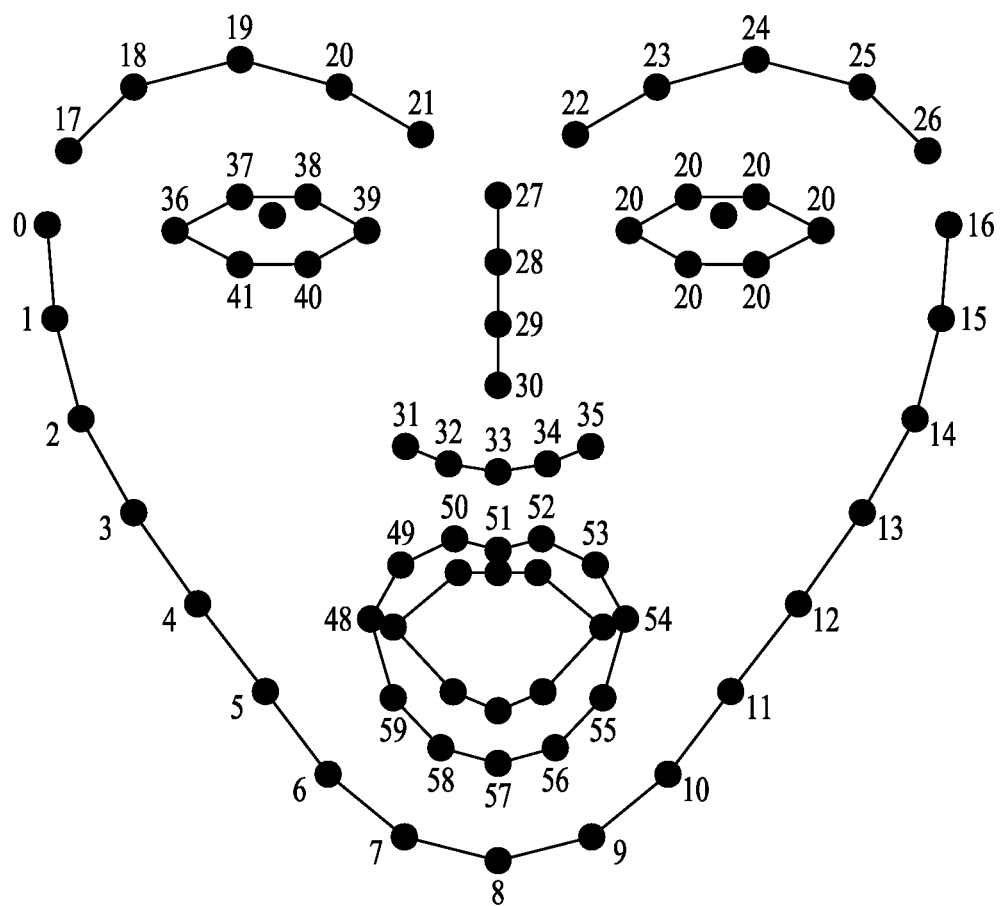
FIG. 18 depicts an example face pose output format, according to an example embodiment.
Figure 19:
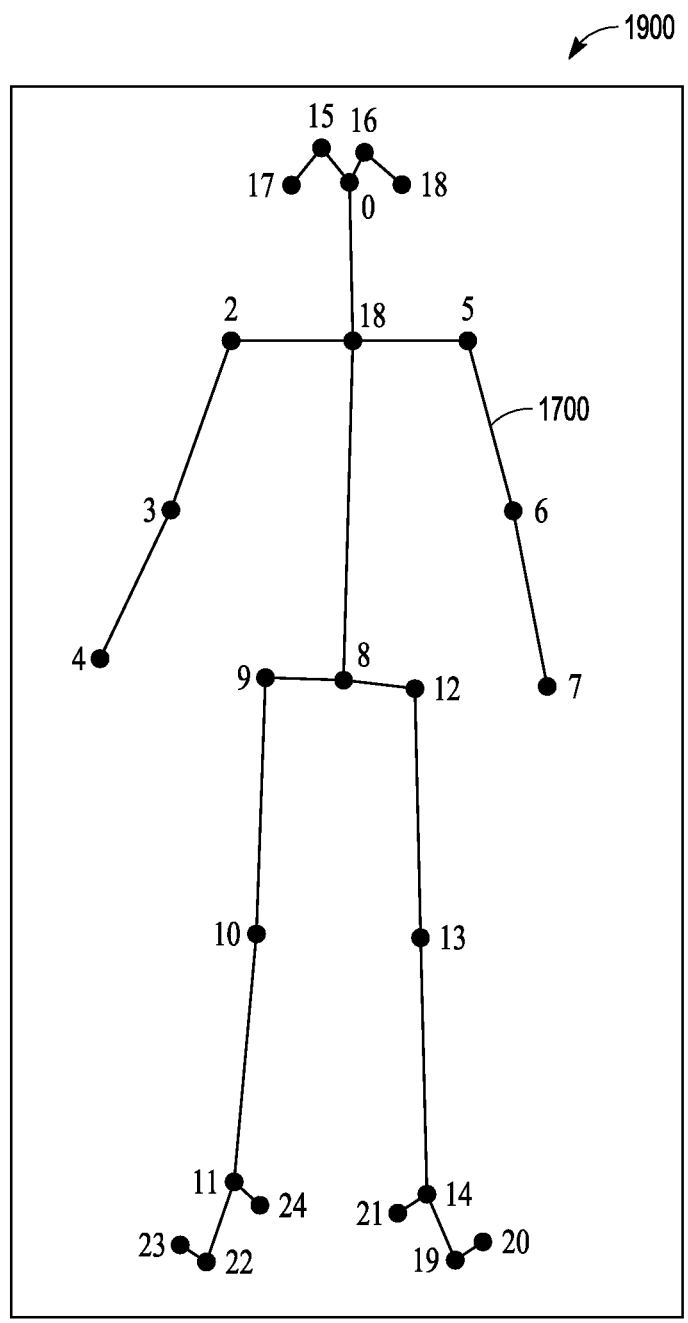
FIG. 19 depicts an example body pose output format, according to an example embodiment.
Figures 20A, 20B, 20C, 20D:
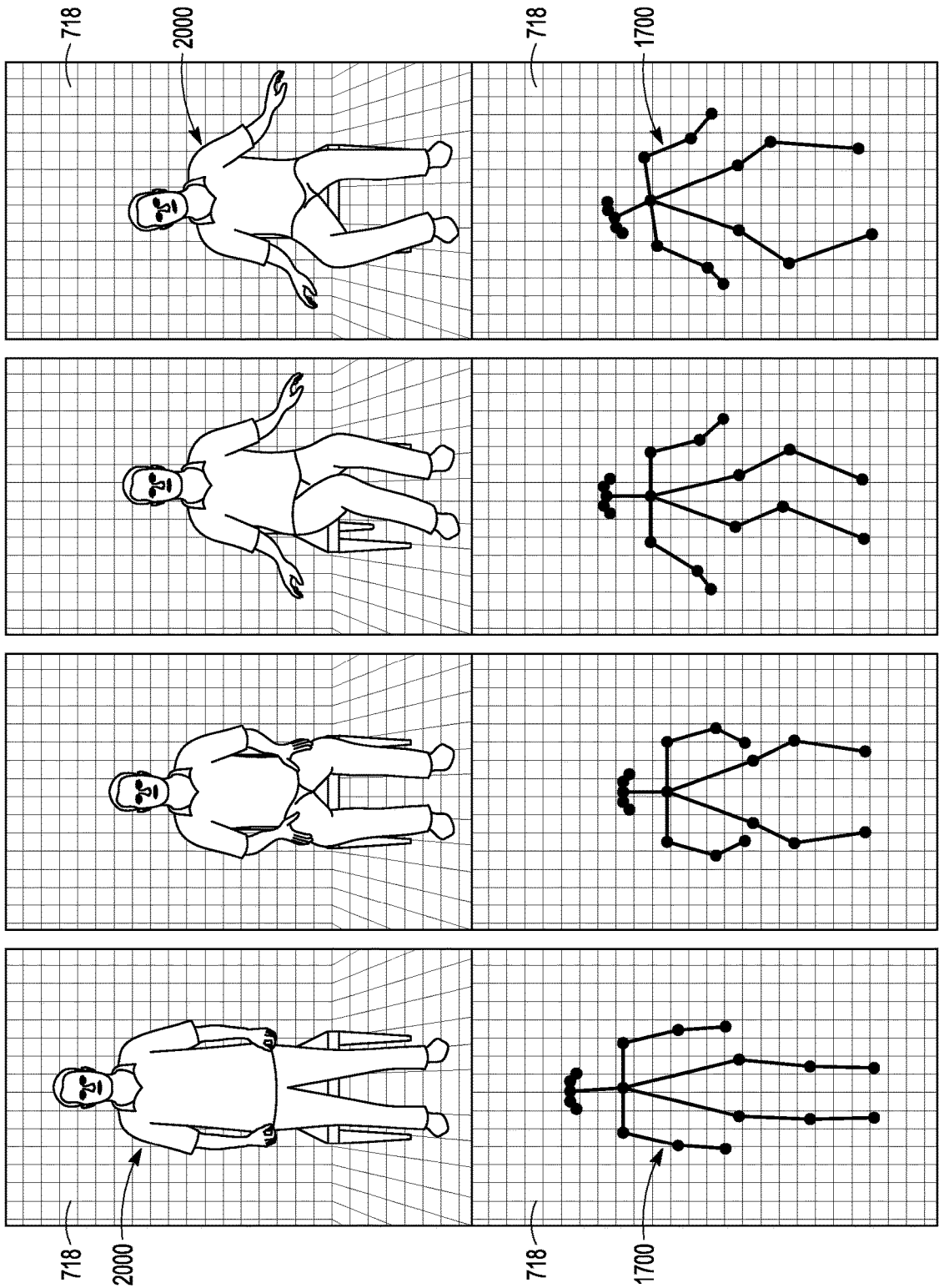
FIGS. 20A-20D represent different poses of a subject alongside extracted skeletons displayed within a measurement or reference grid overlaid images in a video and sized according to a reference scale, according to example embodiments.
Figure 21A:
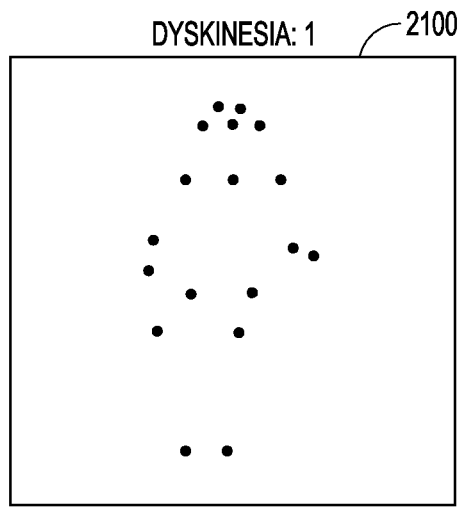
FIGS. 21A-21D depict example movement trajectories of an assessed subject, according to example embodiments.
Figure 21B:
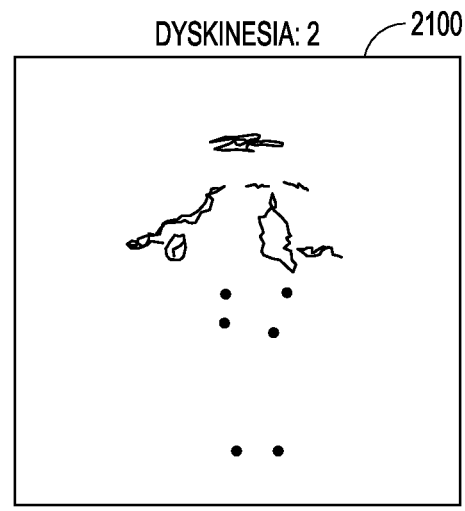
Figure 21C:
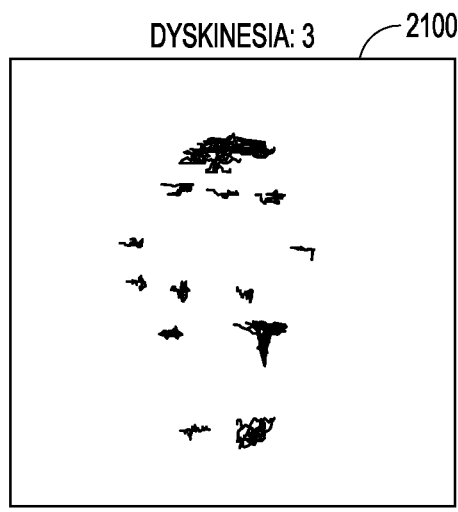
Figure 21D:
Figure 22A:
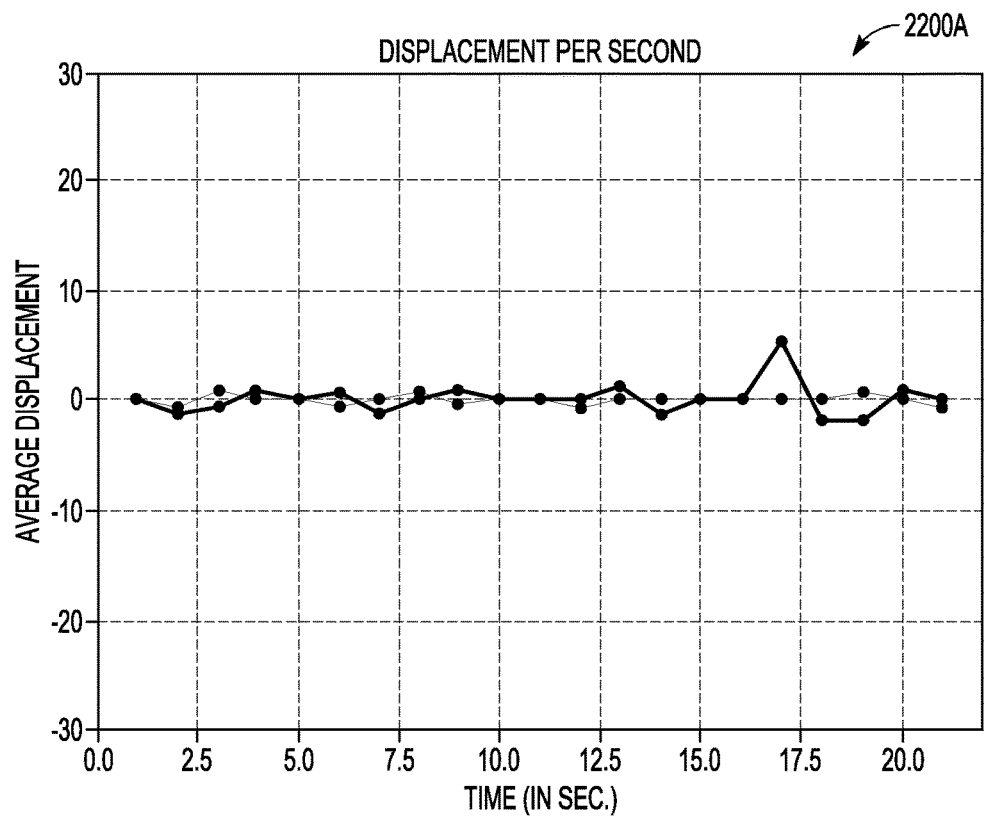
FIGS. 22A-22D depict example graphs with results plotted for x and y displacement of an example neck key point illustrating various levels of dyskinesia, according to example embodiments.
Figure 22B:
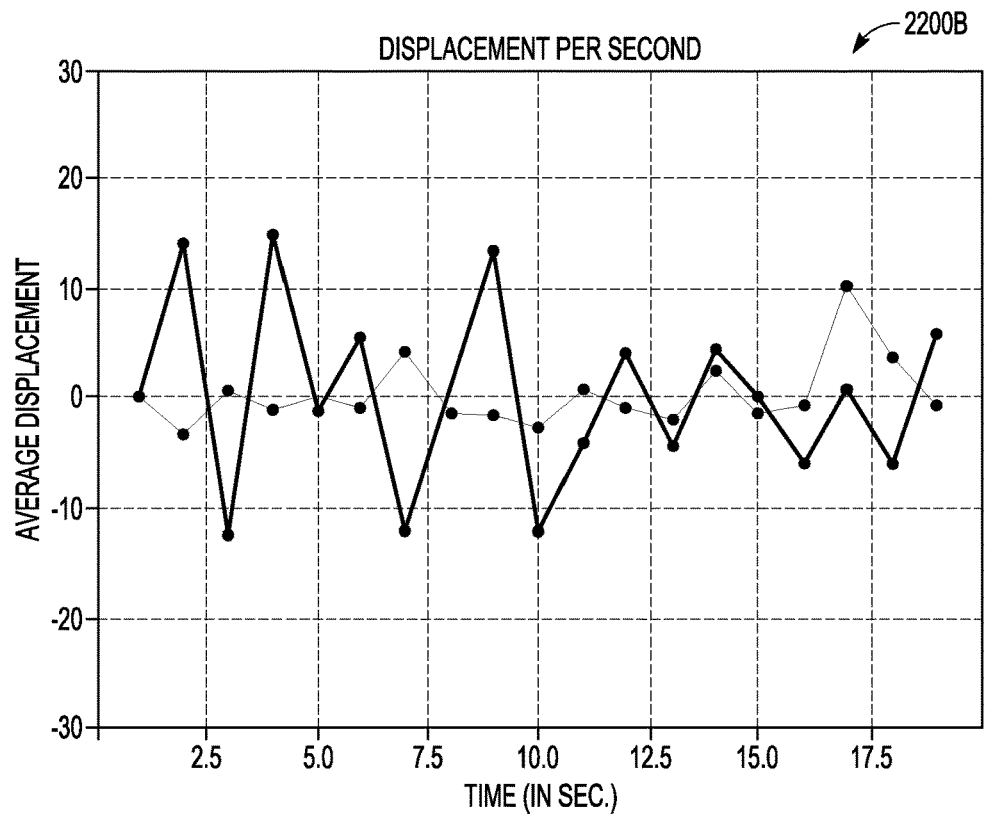
Figure 22C:
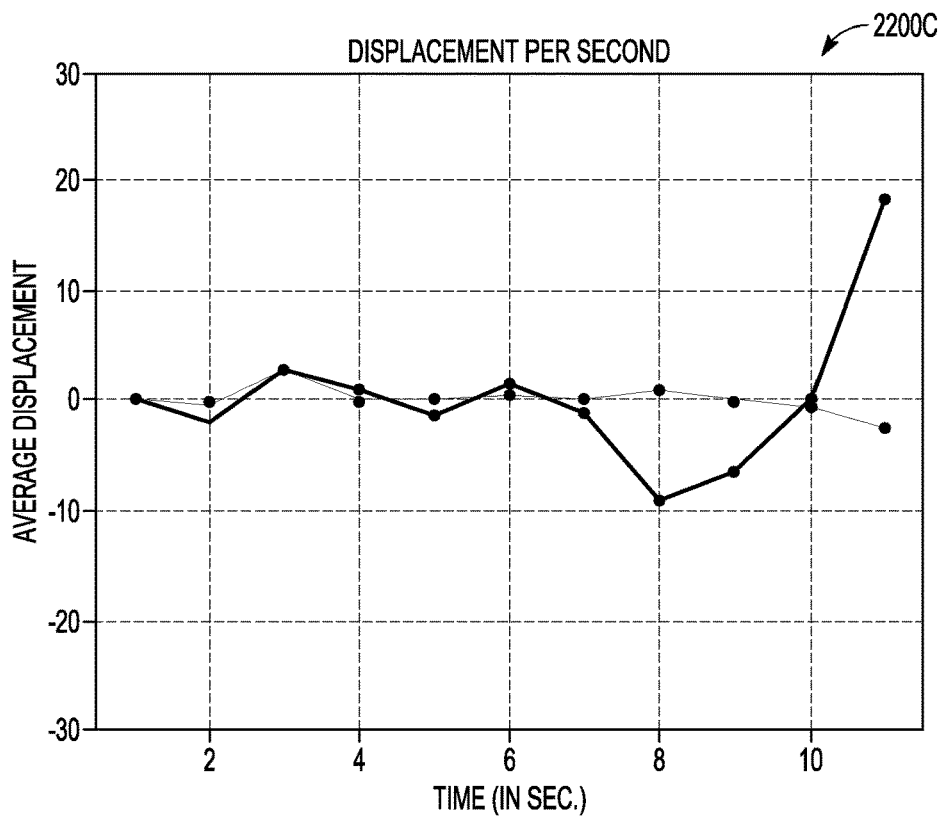
Figure 22D:
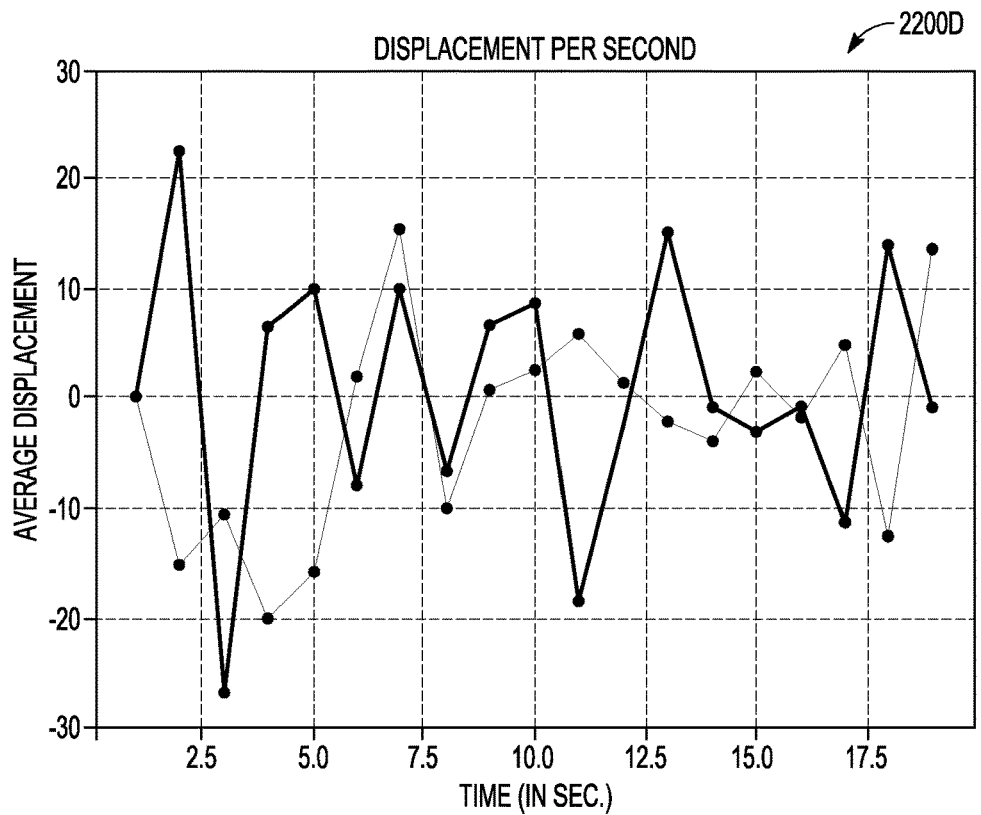
Figure 23A:
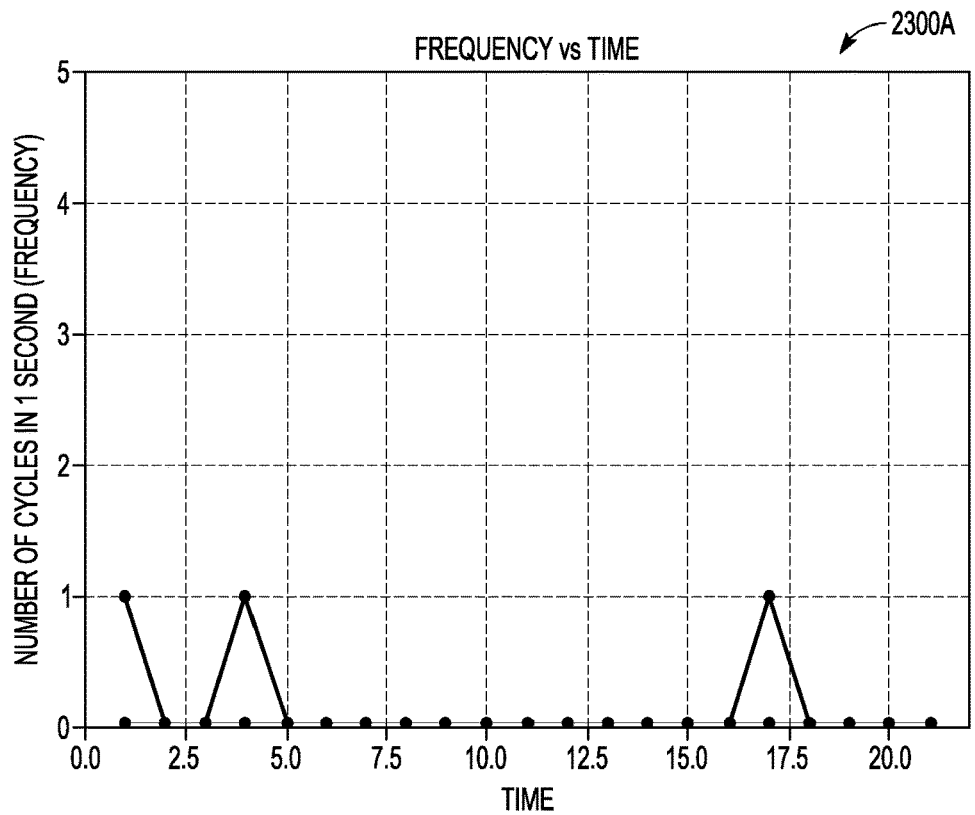
FIGS. 23A-23D depict example graphs with results representing measured frequencies corresponding to different levels of dyskinesia, according to example embodiments.
Figure 23B:
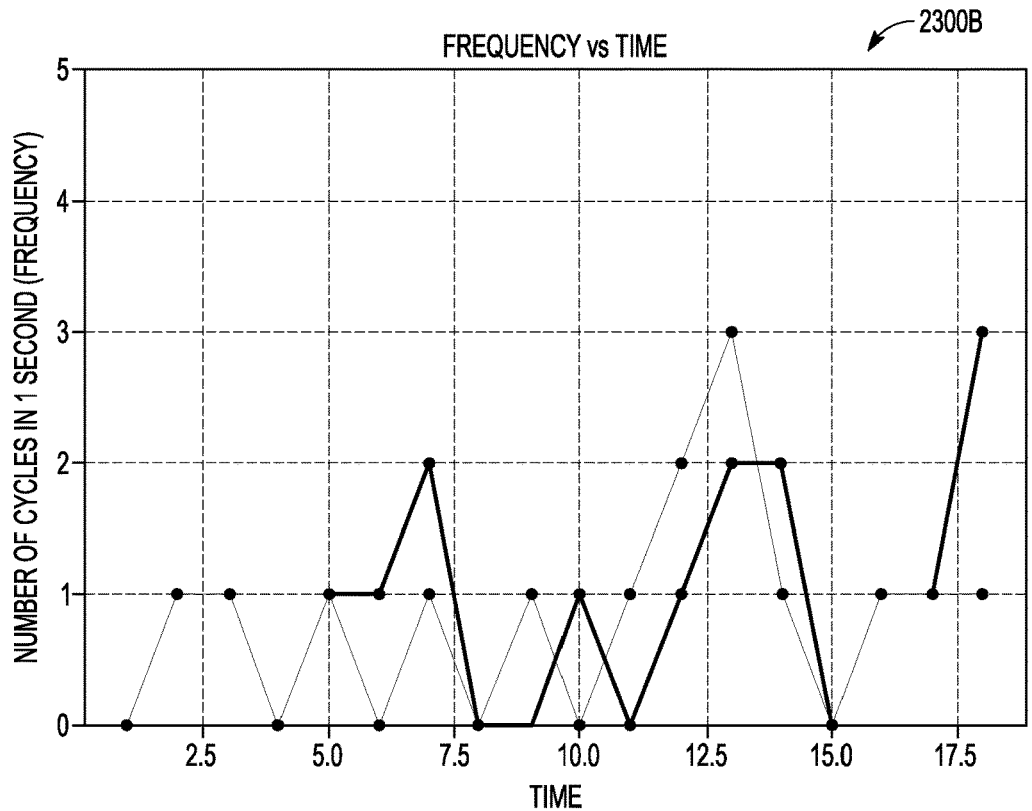
Figure 23C:
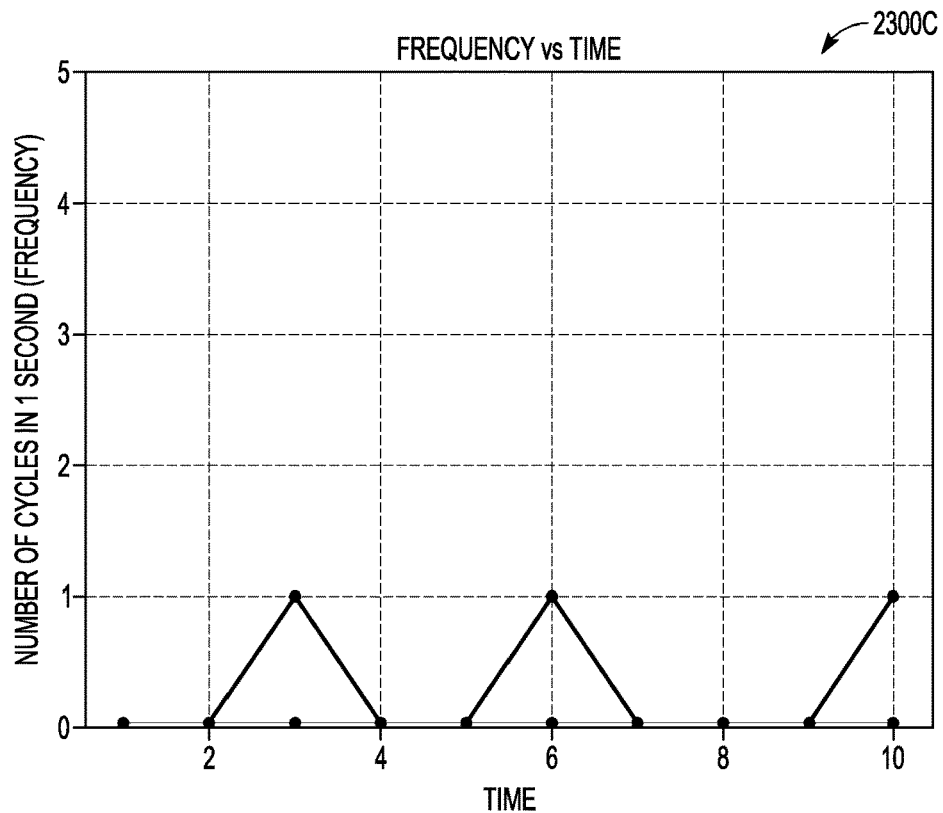
Figure 23D:
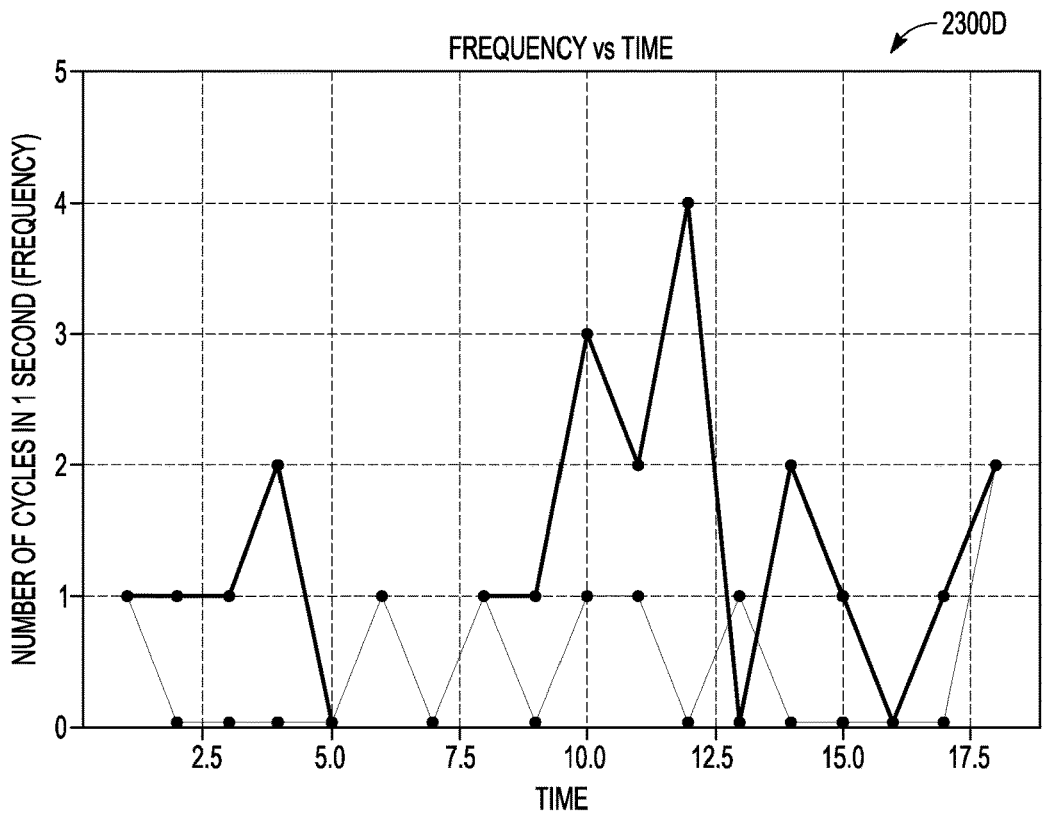

FIG. 18 depicts an example face pose output format 1800 for measured face movement with key points (features) numbered as shown. FIG. 19 depicts an example body pose output format 1800 for body (skeleton 1700) movement assessment with key points (features) numbered as shown. The position of each numbered key point is recorded at each frame and is used to make the aggregate facial or body movement measurements. The displacement and velocity of the key points are used to measure the movement of prospective body parts including for example the neck, the fingers, the hands and legs, and so forth, as depicted in FIGS. 17C-17D, for example.

In some examples, a visualization of face or body movement is performed. Such measurement it typically recorded in pixels. Movement in pixels does not provide a real-world analysis. A movement expressed in pixels is converted to real world units, such as centimeters (cm) for example. In some examples, a conversion to real world scale requires the estimation of a relative scale between pixels and centimeters. An estimation of scale involves various challenges such as a depth estimation which is not possible with mobile phone camera as it typically only includes a single monocular camera which is uncalibrated. Calibration parameters cannot be determined in real-time as each phone has a different camera and a generic calibration across devices is not possible.

To address the issue, in some examples a linear approach is applied. The height in cm and the weight of the patient are known. An image of the patient is taken in which he is standing straight to imitate actual height. This frame is called the reference frame. The height of the patient is mapped to the pixel distance between head to toe to get a relative scale (r). With this relative scale (r), some actual horizontal and vertical distances between key points are stored. Example distances which may be stored are: a distance between the two shoulders, a face width, a height of torso, a length of arm, a length of leg from knee to top and a length of the leg from knee to toe.

However, on occasion it may not be possible to use only one distance as a reference dimension as the associated particular body part may disappear from the frame as the person (or part) moves closer to the camera. Moreover, when a patient is standing perpendicular to the camera facing left or right, the visible horizontal distances may diminish down to a zero value and hence cannot be used as reference. Similarly, if the observed patient bends down, the vertical distances cannot be used as references and hence horizontal distances are determined in some examples to calculate the scale at that point. Thus, the human body itself may be used as a reference to measure the scale of movement at each of several points in a video, thus obviating the need for an independent reference object.

The may provide certain advantages. For example, a reference object cannot be used here for the reason that as the patient moves closer or away from the camera, the reference object cannot be moved along with the patient. The patient is self-calibrating, as it were. Thus, one or more body parts may be used to determine a reference scale.

In some examples, a reference distance (D) and the distance between pixels (d) in a current frame and the distance between the corresponding pixels in a reference frame ($d_{ref}$) are used to calculate a relative scale (r) between a pixel and a real-world scaling system. This relative scale can be used to calculate the movement in the current frame, where:

$$r = \frac{d}{d_{ref}} XD$$

This relative scale is used to measure the movement of pixels in cm. A measured movement expressed in pixels is multiplied by (i.e. scaled up or scaled down) the relative scale (r) to derive a real-world face or measurement. In some examples, the calculated movement in centimeters is used to infer the level of dyskinesia of the patient. With reference to FIGS. 20A-20D, in some examples, a reference scale is used in association with the overlay of a grid 718 in images of a video to approximate measurement of a subject 2000 in a real-world scale. Each box of the grid 718 may be a square of side 10 cm, for example. As the subject 2000 moves toward or away from the camera, the reference scale changes. As the scale changes dynamically, so the grid is changed dynamically, accordingly.

The images in FIGS. 20A-20D represent different poses of a subject 2000 alongside extracted skeletons 1700 displayed within a measurement or reference grid overlaid images in the video and sized according to the reference scale. These depictions may assist in providing a visual understanding of the degree of movement of a subject in real-world scale.

In some examples, distances between key points are used as a reference to measure a scale at each reference point. In such cases, another reference object cannot be used as a reference as the object cannot move along with the patient and the scale changes as the patient moves towards or away from the camera. Here, a distance between adjacent key points may be used as reference instead. In some examples, a measurement system measures original distances between adjacent keyframes in a first video frame with the height of the patient standing and a relative scale is determined according to changes in these original distances. A trajectory of the key points may be plotted to determine a degree of randomness of the assessed facial or body movement.

For example, and with reference to FIGS. 21A-21D, example movement trajectories 2100 of assessed subjects may be displayed, each subject having a different level of dyskinesia in the views. It may also be observed from the images in FIGS. 21A-21D that the randomness in the subject's movement increases as the level of dyskinesia increases. This visualization can help doctors to determine the level of dyskinesia of the subject.

In some examples, measurement of a level of dyskinesia may depend on a number of factors, for example a measurement of the movement displacement, and a measurement of the movement frequency. In order to measure an amplitude of displacement of movement, the movement of each of the key points in both directions, i.e. x and y directions, is tracked. In a particular direction of movement (i.e. x or y), a key point can move in one of two ways i.e. left or right in the x-direction, or up or down in the y-direction. One of the direction is taken as a positive and other direction is taken as negative, and the displacement (amplitude) is measured with respect to a position in the previous second. A net displacement per second is calculated and plotted versus time on a graph.

FIGS. 22A-22D depict example graphs 2200 with results plotted for x and y displacement of an example neck key point illustrating various levels of dyskinesia. The displacement or amplitude of the associated level of dyskinesia increases in the views from FIG. 22A to FIG. 22D. The positive and negative y-axes represent movement in two opposite directions with amplitudes as shown. The various graphs represent displacement on an x-axis and a y-axis. It may be observed from the graphs that maximum displacement increases as the level of dyskinesia increases. This may serve to justify the validity of using displacement as a metric for as assessed degree of dyskinesia.

Turning now to measurement of frequency, in some examples an amplitude of movement at a key point is determined or fixed, and with respect to which a frequency of movement at the key point is established. In some examples, a number of cycles of movement that a key point makes between positive and negative values of the fixed amplitude is measured. In some examples, in order to keep an amplitude fixed, a range of displacement over a complete dataset is analyzed to derive an average amplitude for all levels of dyskinesia. To differentiate between levels of dyskinesia and to provide a metric which may work as a good estimator, a value of Amplitude (A) of a given key point is fixed and a number of cycles the key point makes between −A and +A is determined.

FIGS. 23A-23D depict example graphs 2300 with results representing measured frequencies corresponding to different levels of dyskinesia. The graphs represent the frequency of movement of a neck key point between amplitudes of movement +A and −A. An amplitude A of 25 pixels was used in the illustrated case. It may be observed from the graphs 2300 that the frequency of movement increases with the level of dyskinesia. This may also serve to show that frequency is a helpful metric to establish levels of dyskinesia.

In some examples, the intervention of a human observer is not required to determine a level of dyskinesia. Some examples provide a fully automatic system to determine a level of dyskinesia. Some examples employ a machine learning model which extracts information from pre-processed videos and predicts a level of dyskinesia for a given subject.

An example machine learning model is now described. A set of video clips of subjects having differing levels of dyskinesia was assembled and categorized from 0-4 (no dyskinesia to very serious dyskinesia). In some examples, the frames per second (FPS) value of the video clips in each set were not consistent and required normalization before being placed into a machine learning model.

In some examples, an FPS of 15 was determined to be a relatively balanced value for machine learning purposes. The value was efficient in needing lower levels of computational power only, while remaining stable and informative as the same time.

Some examples included video clip duration normalization. Here, different duration values were assessed for machine learning and it was determined that video clips of 20 seconds in duration carried sufficient movement information for prediction purposes, and so in some examples the final 20 seconds of full video clips were used as preprocessed, normalized training samples.

In some examples, a data generation operation is performed. Here, an extraction tool as described above may be used to detect a patient's key point movement during a test. The movement of all key points of interest per second may be stored into a file. A video of the movement of each key point may have has a specific folder storing all data files for that point. Some examples include a software program for organizing all data folders into a certain format for example by shape and a certain order, and for placing the folders into a file specifically prepared for a machine learning model. Some examples utilize Gaussian normalization to process the training data.

Some examples allow prediction by a machine learning technique. Here, long short term memory (LSTM) may be units of a recurrent neural network (RNN). An RNN composed of LSTM units is typically referred to as an LSTM network. An LSTM unit is composed of a cell, an input gate, an output gate and a forget gate. The cell remembers values over arbitrary time intervals and the three gates regulate the flow of information into and out of the cell.

In example training operations, preprocessed data files as discussed above for example are placed into an LSTM model. After a period of training, for example two days, the model may reach approximately 100% accuracy for the collected set of video clips. In some examples, testing is created for predicting measurement results in videos in the real world. If the predicted results do not match actual scores derived for a given patient, this may indicate that further training for a machine model is required for higher accuracy.

Figure 24:
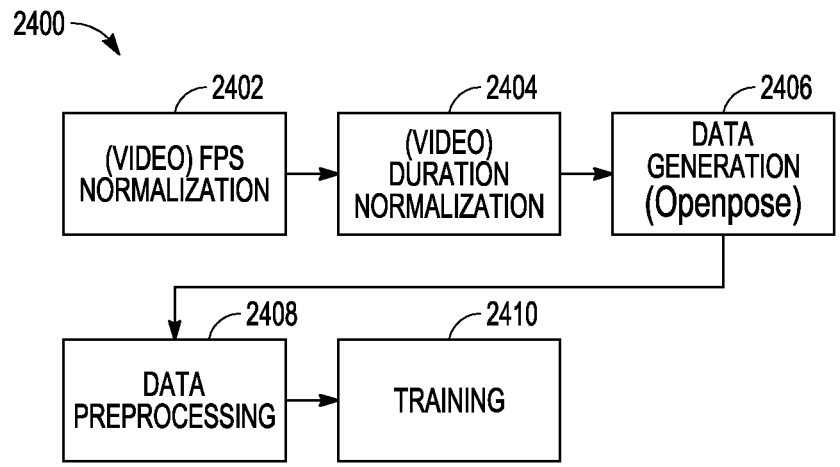
FIGS. 24-25 depict example operations in methods, according to example embodiments.
Figure 25:
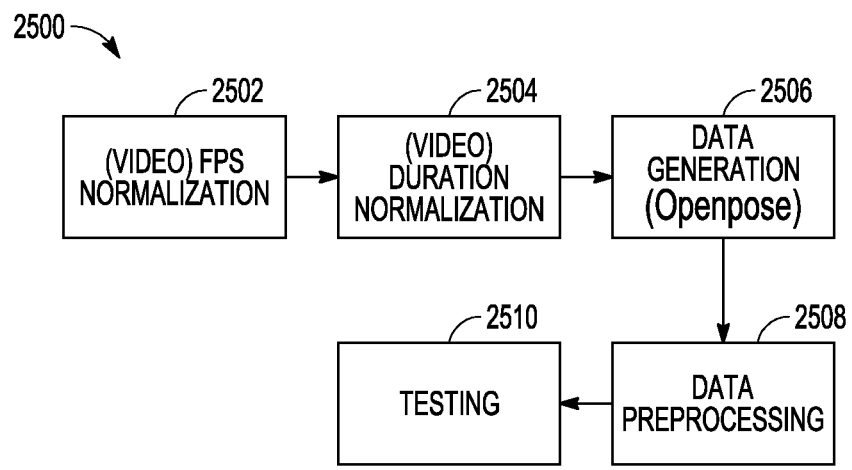

Example operations in a machine learning process may include those shown in FIGS. 24-25. For example, operations in a machine training process 2400 (FIG. 24) may include: at 2402, video FPS normalization; at 2404, video clip duration normalization; at 2406, data generation, at 2408, data preprocessing, and at 2410, machine training. Example operations in a process 2500 (FIG. 25) for testing a trained model may include: at 2502, video FPS normalization; at 2504, video duration normalization; at 2506, data generation; at 2508, data preprocessing; and, at 2510, model testing.

Figure 26:
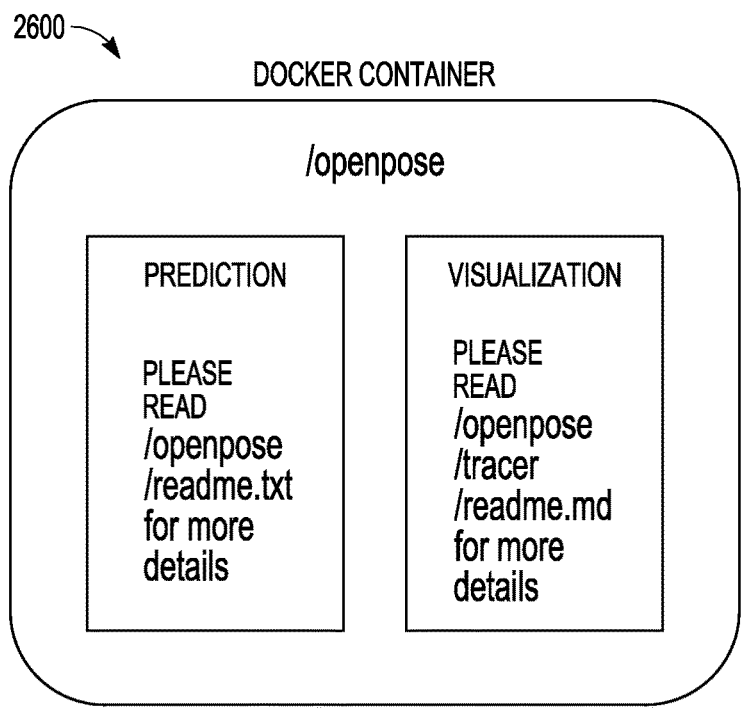
FIGS. 26-27 depict example architectures, according to example embodiments.
Figure 27:
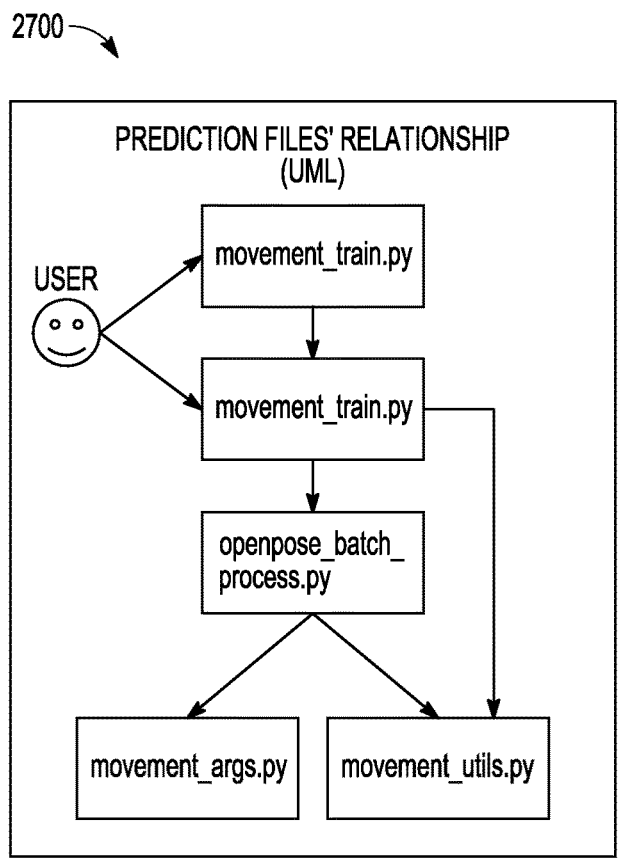

An example architecture 2600 of a training program may include the components shown in FIG. 26. An example architecture 2700 for components in a prediction process are shown in FIG. 27.

Figure 28:
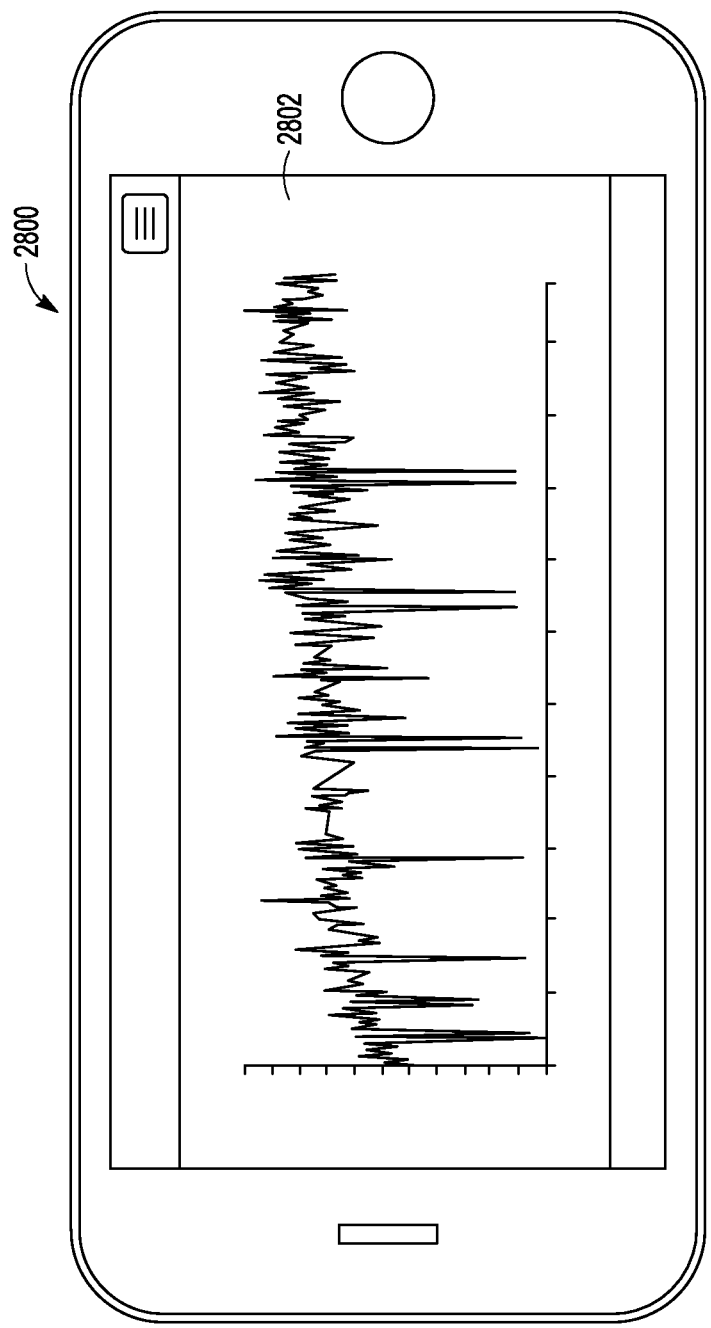
FIGS. 28, 29, 30A, 30B and 31 illustrate further aspects of body movement measurement, according to example embodiments.

With reference to FIG. 28, an example system of the present disclosure combines exercise with mobile software on a smart device 2800 (for example, an application such as pdFIT) to provide coaching and biofeedback 2802 in order to improve Parkinson's disease symptoms and delay disease progression. A two-year study showed that subjects who use pdFIT regularly had statistically-significantly improvement in their motor control over the entire study period.

Medication/Symptom Tracking

Figure 29:
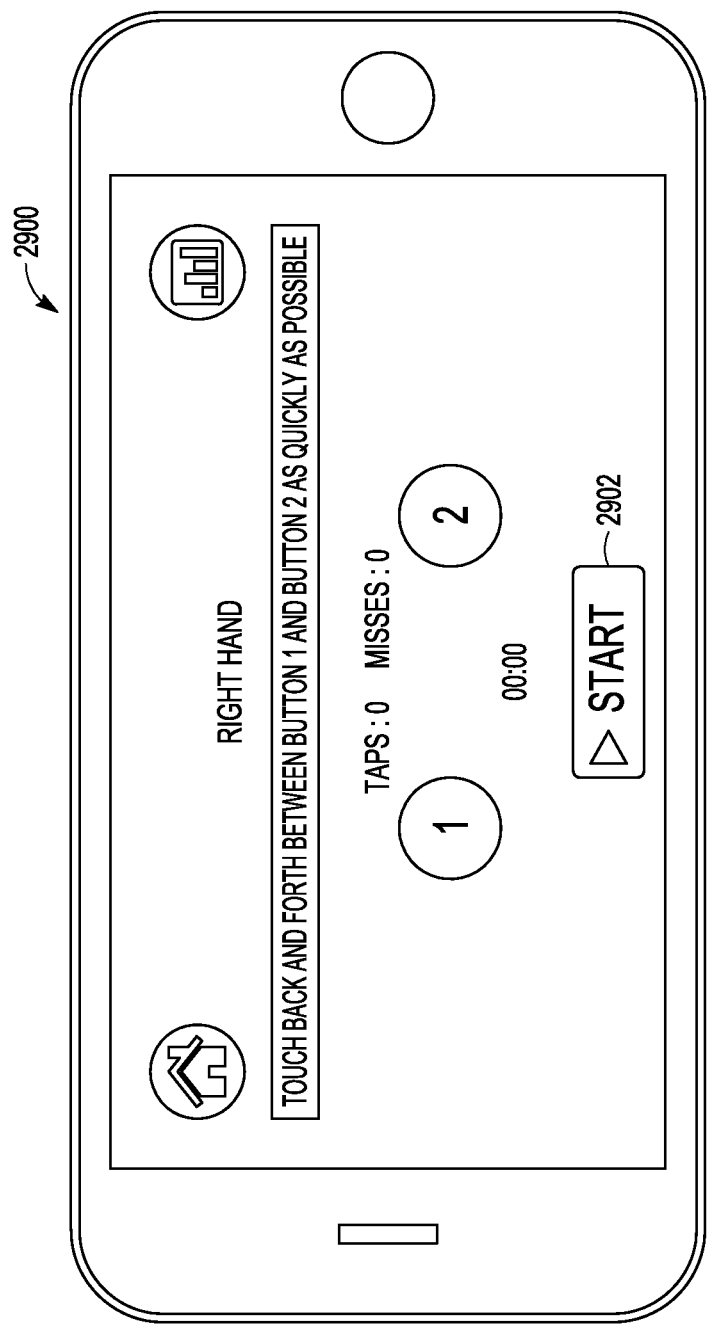

With reference to FIG. 29, medication reminders may help subjects become more adherent to their treatment plans which improves outcomes. By layering objective outcome measures (such as the results of a series of tap tests 2902 conducted via the screen of a smart device 2900 for example), over a subject's medication dosage or timing regimen, a subject can be made increasingly aware of how movement disorder symptoms change hour-to-hour and over time. Sharing this information with a physician may result in a more informed treatment plan.

Before and after Intraday Medication/Symptom Charts

Figure 30A:
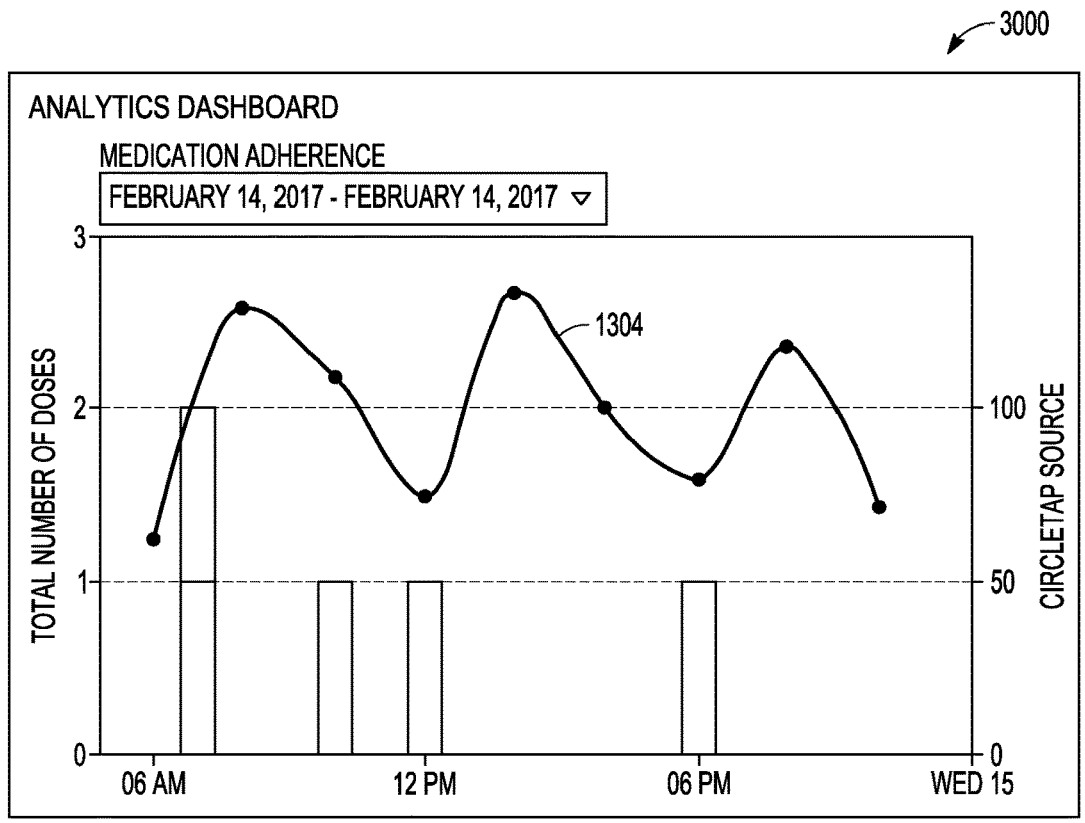
Figure 30B:
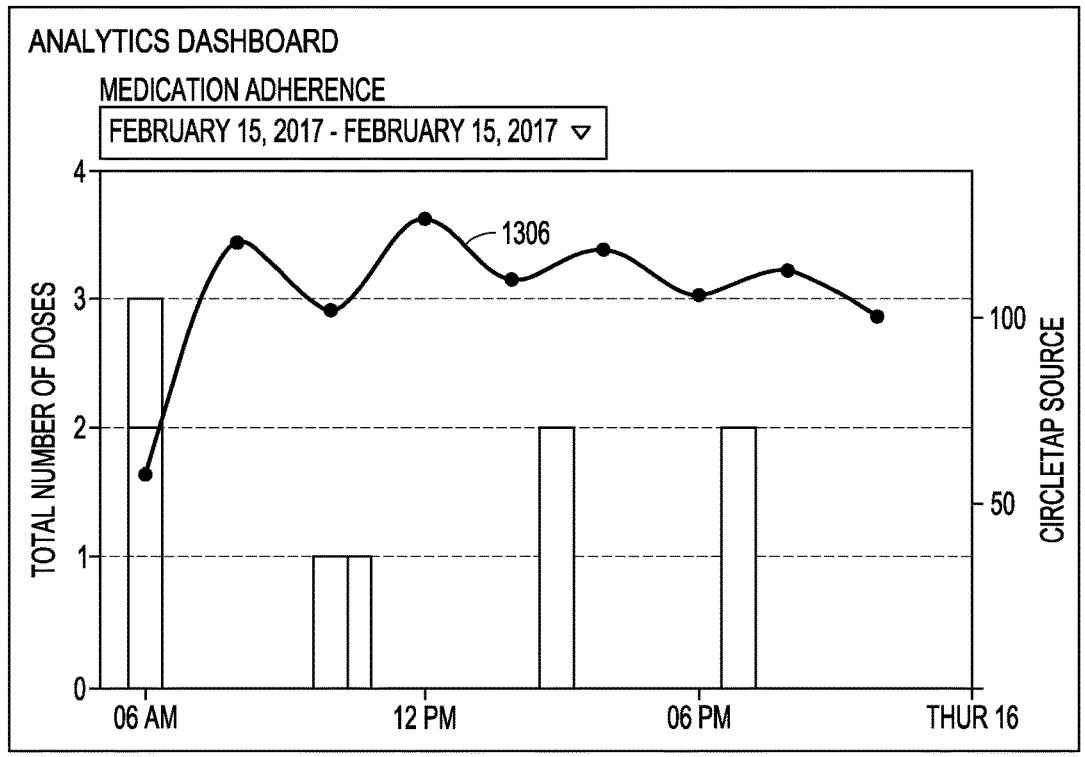

One of the challenges for a subject managing Parkinson's disease is understanding the timing and severity of their symptoms and how they respond to medications. For example, Levodopa is a medication that has a positive effect on motor symptoms but becomes less effective over time and usually causes additional symptoms such as dyskinesia and psychosis. Off episodes or off-time are the periods of a day when Levodopa's effectiveness wanes and symptoms such as bradykinesia and tremor make functioning difficult. With reference to FIGS. 30A-30B, the charts 3000 and 3002 illustrate how understanding motor control symptoms and medication dose/timing during a day can influence treatment plans. The undulating lines 3004 and 3006 in each chart represent a subject's finger tapping test scores, for example.

In a before-medication chart 3000, the line 3004 is representative of major fluctuations in the subject's motor control. The troughs of the red line 3004 represent subject off time. This may indicate or be caused by the subject taking three doses of Levodopa per day, for example. In the after-medication chart 3002, the example treatment plan was changed to four doses a day of extended release Levodopa. The flattening of the motor control line 1306 represents an elimination of patient off-time.

Symptom/Medication Longitudinal Chart

It may be important for patients and care givers to understand how medication is affecting symptoms and how the disease is progressing. Armed with longitudinal medication and symptom data, a PwP is empowered to influence their treatment plans. In addition to being more engaged in their situation through symptom tracking, the tools of the present disclosure help to improve outcomes by helping subjects be more adherent to their medication regimen.

Figure 31:
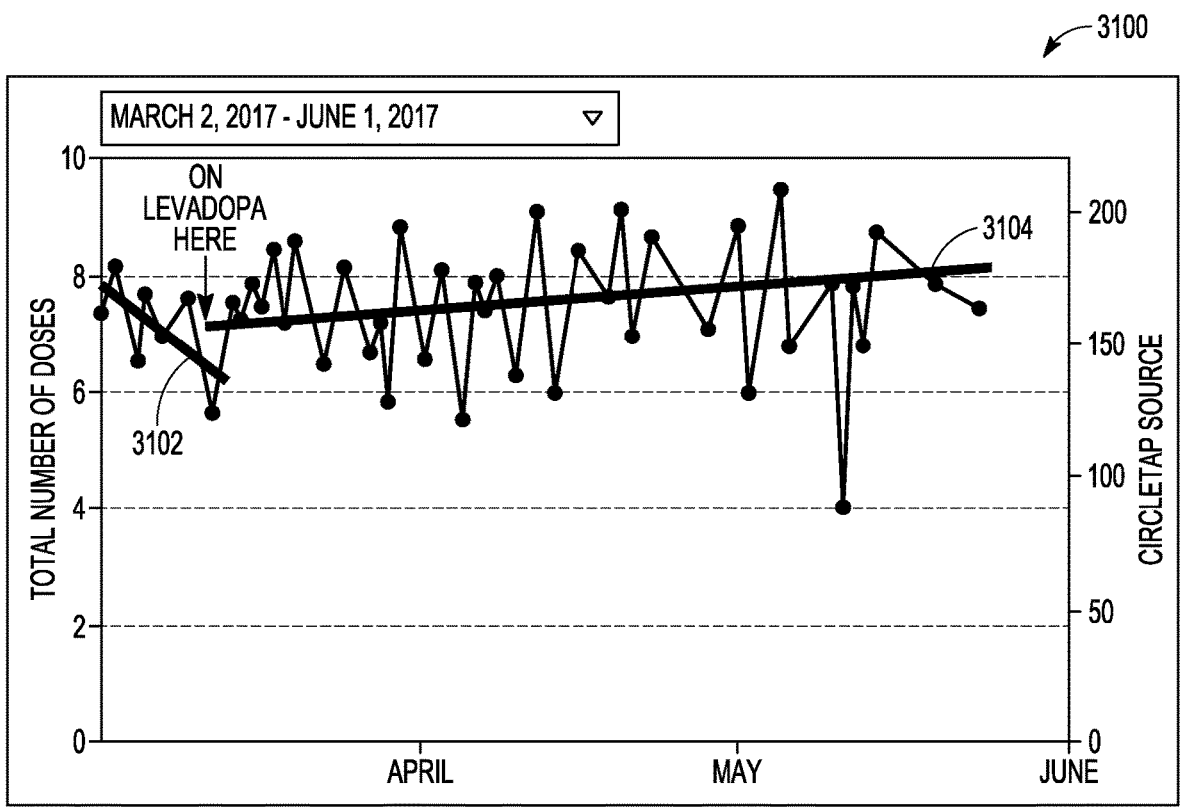

With reference to FIG. 31, the illustrated chart 3100 indicates results of movement disorder testing in an example embodiment. Here, a subject's motor control is getting worse during the first two weeks of the test period as depicted by the first trend line 3102, for example. The subject was then placed on Levodopa medication. This change in treatment plan resulted in an immediate and dramatic improvement in motor control as seen by the individual finger tapping scores immediately following the introduction of Levodopa. This is depicted by the second trend line 3104. The trend line 3104 extends out a couple months and denotes a sustained and gradual improvement in motor control.

Symptom Complexity

Parkinson's disease is also known as a "snowflake disease" because each instance is unique to the individual. In addition to motor control issues such as tremors rigidity, bradykinesia, postural instability, gait issues and vocal issues, PwP are also affected with non-motor symptoms such as cognitive changes, sleep disorders, depression, anxiety, hallucinations and delusions, fatigue, hypotension, sexual concerns and vision issues.

The most effective PD medication is Levodopa which is converted to dopamine in the brain. Unfortunately, Levodopa is directly responsible for the introduction of additional symptoms that require management. These symptoms include dyskinesia, psychosis and impulse-control disorder (binge eating, excessive shopping and gambling, hypersexuality). Many newly-approved and Phase 3 medications address Levodopa-induced side effects.

Levodopa and Dyskinesia

Early-stage patients are more easily managed on Levodopa. Levodopa remains as the most effective treatment for PD, and over 75% of the patients with PD receive Levodopa. However, long term treatment with Levodopa leads to seriously debilitating motor fluctuations, i.e. phases of normal functioning (ON-time) and decreased functioning (OFF-time).

Furthermore, as a result of the use of high doses of Levodopa with increasing severity of the disease, many patients experience involuntary movements known as Levodopa-Induced Dyskinesia (LID). As the disease progresses, more drugs are used as an add-on to what the patient already takes, and the focus is to treat symptoms while managing LID and the "off-time" effects of Levodopa.

Most current therapies target the dopaminergic system that is implicated in the pathogenesis of PD, and most current treatments act by increasing dopaminergic transmission that leads to amelioration of motor symptoms. In addition to being more engaged in their situation through symptom tracking, the tools of the present disclosure improve outcomes by helping subjects be more adherent to their medication regimen.

Thus, in some embodiments, there is provided a system for measuring body movement in movement disorder disease, the system comprising: at least one processor and a memory storing processor executable codes, which, when implemented by the at least one processor, cause the system to perform operations comprising, at least: receiving a video including a sequence of images; detecting at least one object of interest in one or more of the images; locating feature reference points of the at least one object of interest; generating a virtual movement-detection framework in one or more of the images; detecting, over the sequence of images, at least one singular or reciprocating movement of the feature reference point relative to the virtual movement-detection framework; and generating a virtual path tracking a path of the at least one detected singular or reciprocating movement of the feature reference point.

In some embodiments, the operations may further comprise positioning or aligning the virtual movement-detection framework with the at least one object of interest in one or more of the images based at least in part on a feature reference point. In some embodiments, the operations further comprise analyzing coordinates of the virtual path or feature reference point to derive an amplitude of the at least one singular or reciprocating movement of the feature reference point.

In some embodiments, the operations further comprise analyzing coordinates of the virtual path or feature reference point to derive a frequency of the at least one singular or reciprocating movement of the feature reference point. In some embodiments, the operations further comprise associating the detected at least one singular or reciprocating movement, or the virtual path, with a body movement disorder selected from a plurality of body movement disorders. In some embodiments, the operations further comprise generating or presenting a disorder status of an individual based on the associated body movement disorder selected from the plurality of body movement disorders.

In some embodiments, the operations further comprise transmitting a communication including data associated with the disorder status based on or including a trend in the disorder status.

Figure 32:
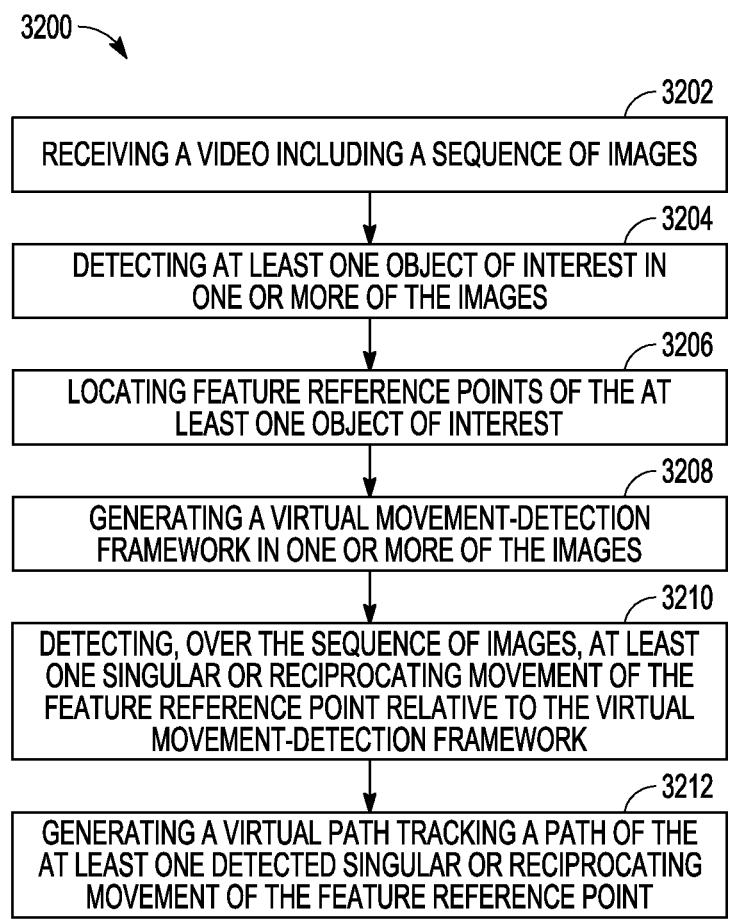
FIG. 32 is a flowchart of operations in a method, according to an example embodiment.

Some embodiments of the present disclosure include method embodiments. With reference to FIG. 32, a method 3200 may comprise: at 3202, receiving a video including a sequence of images; at 3204, detecting at least one object of interest in one or more of the images; at 3206, locating feature reference points of the at least one object of interest; at 3208, generating a virtual movement-detection framework in one or more of the images; at 3210, detecting, over the sequence of images, at least one singular or reciprocating movement of the feature reference point relative to the virtual movement-detection framework; and, at 3212, generating a virtual path tracking a path of the at least one detected singular or reciprocating movement of the feature reference point.

The method 3200 may further comprise positioning or aligning the virtual movement-detection framework with the at least one object of interest in one or more of the images based at least in part on a feature reference point.

The method 3200 may further comprise analyzing coordinates of the virtual path or feature reference point to derive an amplitude of the at least one singular or reciprocating movement of the feature reference point.

The method 3200 may further comprise analyzing coordinates of the virtual path or feature reference point to derive a frequency of the at least one singular or reciprocating movement of the feature reference point.

The method 3200 may further comprise associating the detected at least one singular or reciprocating movement, or the virtual path, with a body movement disorder selected from a plurality of body movement disorders.

The method 3200 may further comprise generating or presenting a disorder status of an individual based on the associated body movement disorder selected from the plurality of body movement disorders.

The method 3200 may further comprise transmitting a communication including data associated with the disorder status based on or including a trend in the disorder status.

Example embodiments also include machine-readable media including instructions which, when read by a machine, cause the machine to perform operations comprising at least those summarized above, or described elsewhere herein.

Although the subject matter has been described with reference to specific example embodiments, it will be evident that various modifications and changes may be made to these embodiments without departing from the broader spirit and scope of the disclosed subject matter. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Description, therefore, is not to be taken in a limiting sense, and the scope of various embodiments is defined only by any appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for measuring body movement in movement disorder disease, the system comprising:
at least one processor and a memory storing processor executable codes, which, when implemented by the at least one processor, cause the system to perform operations comprising, at least:
receiving a video including a sequence of images;
detecting at least one object of interest in one or more of the images;
locating feature reference points of the at least one object of interest;
generating a fixed virtual movement-detection reference framework in one or more of the images;
detecting, over the sequence of images, at least one singular or reciprocating movement of the feature reference point relative to the fixed virtual movement-detection reference framework; and
generating a virtual path tracking a path of the at least one detected singular or reciprocating movement of the feature reference point.

2. The system of claim 1, wherein the operations further comprise:
positioning or aligning the fixed virtual movement-detection reference framework with the at least one object of interest in one or more of the images based at least in part on a feature reference point.

3. The system of claim 1, wherein the operations further comprise:
analyzing coordinates of the virtual path or feature reference point to derive an amplitude of the at least one singular or reciprocating movement of the feature reference point.

4. The system of claim 1, wherein the operations further comprise:
analyzing coordinates of the virtual path or feature reference point to derive a frequency of the at least one singular or reciprocating movement of the feature reference point.

5. The system of claim 1, wherein the operations further comprise:
associating the detected at least one singular or reciprocating movement, or the virtual path, with a body movement disorder selected from a plurality of body movement disorders.

6. The system of claim 5, wherein the operations further comprise:
generating or presenting a disorder status of an individual based on the associated body movement disorder selected from the plurality of body movement disorders.

7. The system of claim 6, wherein the operations further comprise:
transmitting a communication including data associated with the disorder status based on or including a trend in the disorder status.

8. A method comprising:
receiving a video including a sequence of images;
detecting at least one object of interest in one or more of the images;
locating feature reference points of the at least one object of interest, generating a fixed virtual movement-detection reference framework in one or more of the images;
detecting, over the sequence of images, at least one singular or reciprocating movement of the feature reference point relative to the fixed virtual movement-detection reference framework; and
generating a virtual path tracking a path of the at least one detected singular or reciprocating movement of the feature reference point.

9. The method of claim 8, further comprising:
positioning or aligning the fixed virtual movement-detection reference framework with the at least one object of interest in one or more of the images based at least in part on a feature reference point.

10. The method of claim 8, further comprising:
analyzing coordinates of the virtual path or feature reference point to derive an amplitude of the at least one singular or reciprocating movement of the feature reference point.

11. The method of claim 8, further comprising:
analyzing coordinates of the virtual path or feature reference point to derive a frequency of the at least one singular or reciprocating movement of the feature reference point.

12. The method of claim 8, further comprising:
associating the detected at least one singular or reciprocating movement, or the virtual path, with a body movement disorder selected from a plurality of body movement disorders.

13. The method of claim 12, further comprising:
generating or presenting a disorder status of an individual based on the associated body movement disorder selected from the plurality of body movement disorders.

14. The method of claim 13, further comprising:
transmitting a communication including data associated with the disorder status based on or including a trend in the disorder status.

15. A machine-readable medium including instructions which, when read by a machine, cause the machine to perform operations including, at least:
receiving a video including a sequence of images;
detecting at least one object of interest in one or more of the images;
locating feature reference points of the at least one object of interest;
generating a fixed virtual movement-detection reference framework in one or more of the images;
detecting, over the sequence of images, at least one singular or reciprocating movement of the feature reference point relative to the fixed virtual movement-detection reference framework; and
generating a virtual path tracking a path of the at least one detected singular or reciprocating movement of the feature reference point.

16. The medium of claim 15, wherein the operations further comprise:
positioning or aligning the fixed virtual movement-detection reference framework with the at least one object of interest in one or more of the images based at least in part on a feature reference point.

17. The medium of claim 15, wherein the operations further comprise:
analyzing coordinates of the virtual path or feature reference point to derive an amplitude of the at least one singular or reciprocating movement of the feature reference point.

18. The medium of claim 15, wherein the operations further comprise:

analyzing coordinates of the virtual path or feature reference point to derive a frequency of the at least one singular or reciprocating movement of the feature reference point.

19. The medium of claim 15, wherein the operations further comprise:
associating the detected at least one singular or reciprocating movement, or the virtual path, with a body movement disorder selected from a plurality of body movement disorders.

20. The medium of claim 19, wherein the operations further comprise:
generating or presenting a disorder status of an individual based on the associated body movement disorder selected from the plurality of body movement disorders.

* * * * *